United States Patent
Ikelaar et al.

(10) Patent No.: US 10,987,029 B1
(45) Date of Patent: Apr. 27, 2021

(54) GRAPHICAL USER INTERFACE OF MOBILE DEVICE FOR IMPROVING INTERACTION WITH A PROSTHETIC OR ORTHOTIC DEVICE

(71) Applicant: Össur Iceland ehf, Reykjavík (IS)

(72) Inventors: Lucas Ikelaar, Reykjavík (IS); Matthias Mar Olafs Kristjansson, Reykjavík (IS); Helgi Tomas Hall, Mosfellsbaer (IS)

(73) Assignee: Össur Iceland ehf, Reykjavik (IS)

( * ) Notice: Subject to any disclaimer, the term of this patent is extended or adjusted under 35 U.S.C. 154(b) by 357 days.

(21) Appl. No.: 15/944,460

(22) Filed: Apr. 3, 2018

(51) Int. Cl.
*A61B 5/00* (2006.01)
*A61B 5/11* (2006.01)
*A61F 2/60* (2006.01)
*G16H 20/30* (2018.01)

(52) U.S. Cl.
CPC ............ *A61B 5/112* (2013.01); *A61F 2/60* (2013.01); *G16H 20/30* (2018.01)

(58) Field of Classification Search
CPC ......... A61B 5/11; A61B 5/112; A61B 5/1121; A61F 2/60; A61F 2/64; G16H 20/30
See application file for complete search history.

(56) References Cited

U.S. PATENT DOCUMENTS

| | | | |
|---|---|---|---|
| 8,268,012 B1* | 9/2012 | Cheng | A61F 2/644 623/44 |
| 8,870,968 B2* | 10/2014 | Vo | A61F 2/60 623/32 |
| 2009/0030530 A1* | 1/2009 | Martin | A61B 5/4851 623/53 |
| 2009/0240171 A1* | 9/2009 | Morris Bamberg | A43B 3/0005 600/595 |
| 2010/0131113 A1* | 5/2010 | Even-Zohar | A61F 2/70 700/279 |
| 2013/0190896 A1* | 7/2013 | Brockl | A61F 2/64 623/43 |
| 2017/0076619 A1* | 3/2017 | Wallach | G09B 19/0038 |

\* cited by examiner

*Primary Examiner* — Max F Hindenburg
(74) *Attorney, Agent, or Firm* — Knobbe, Martens, Olson & Bear, LLP

(57) ABSTRACT

Systems and methods for improving an interaction between a prosthetic and/or orthotic device (POD) and a user of the POD are described. In some cases, the POD monitors various parameters during gait and communicates the gait parameters to a remote monitoring device. The remote monitoring device can analyze the gait parameters in real-time to provide various indications of user-POD interactions including, but not limited to, symmetric weight bearing, rolling over the toe, sitting down, stair descent, and/or stair ascent. The remote monitoring device can further provide indications to improve the user-POD interactions.

20 Claims, 19 Drawing Sheets

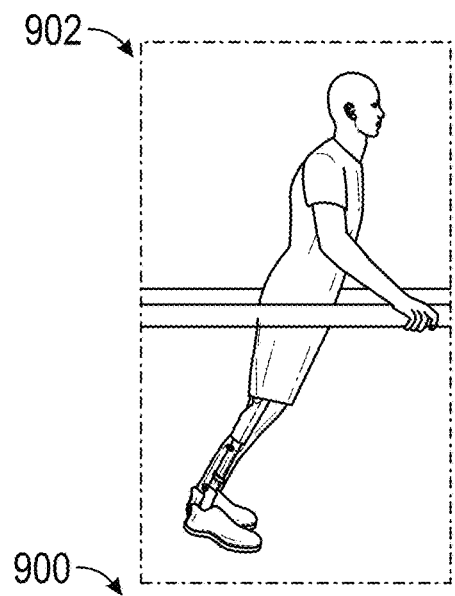
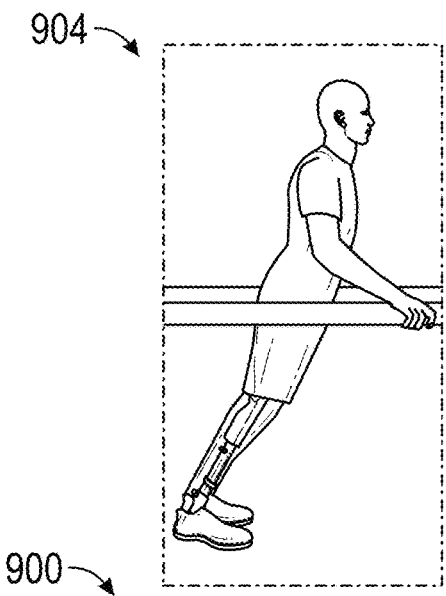
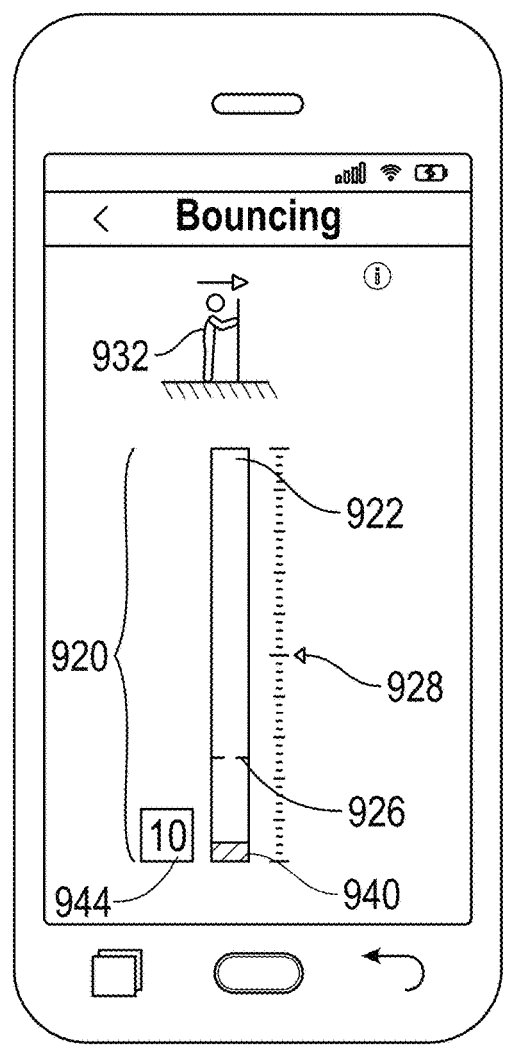
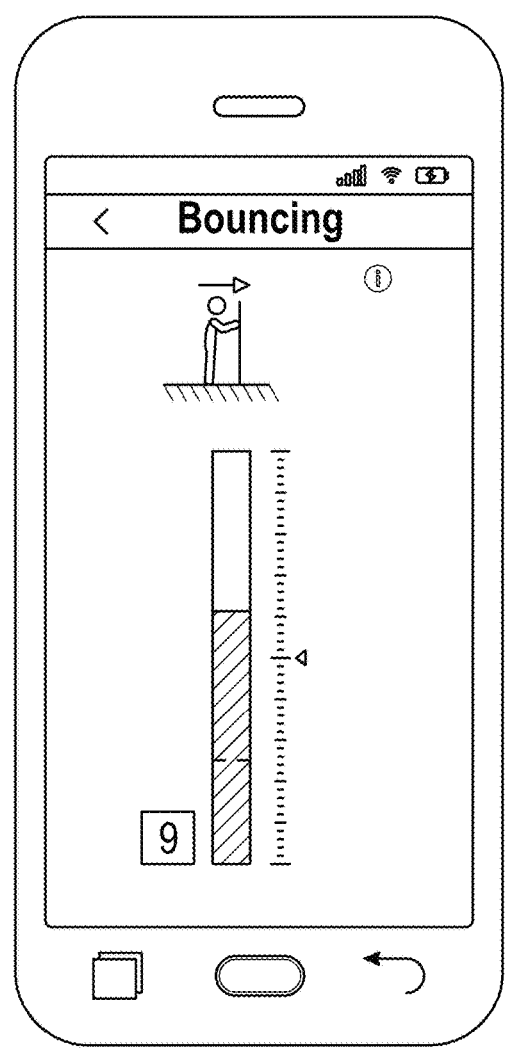
FIG. 9A  FIG. 9B

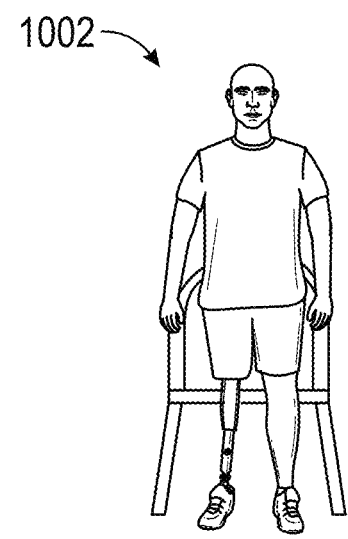
1002
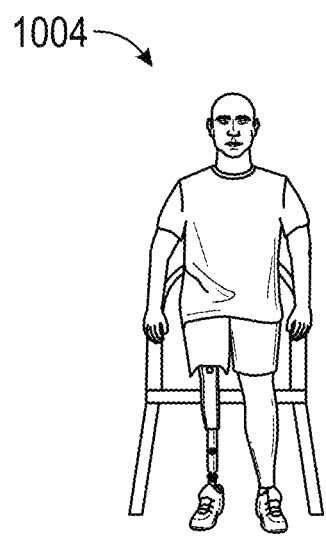
1004
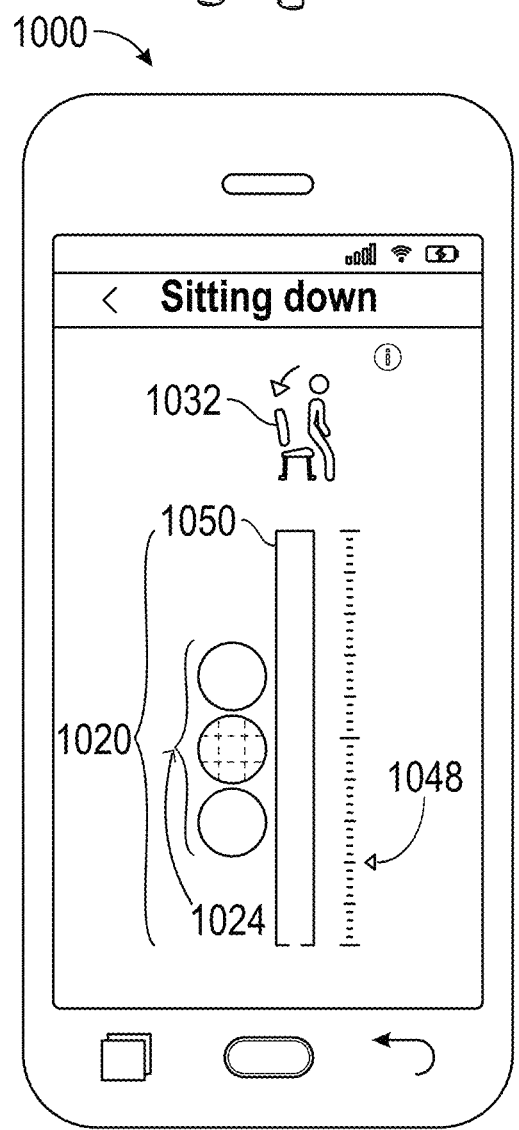
1000
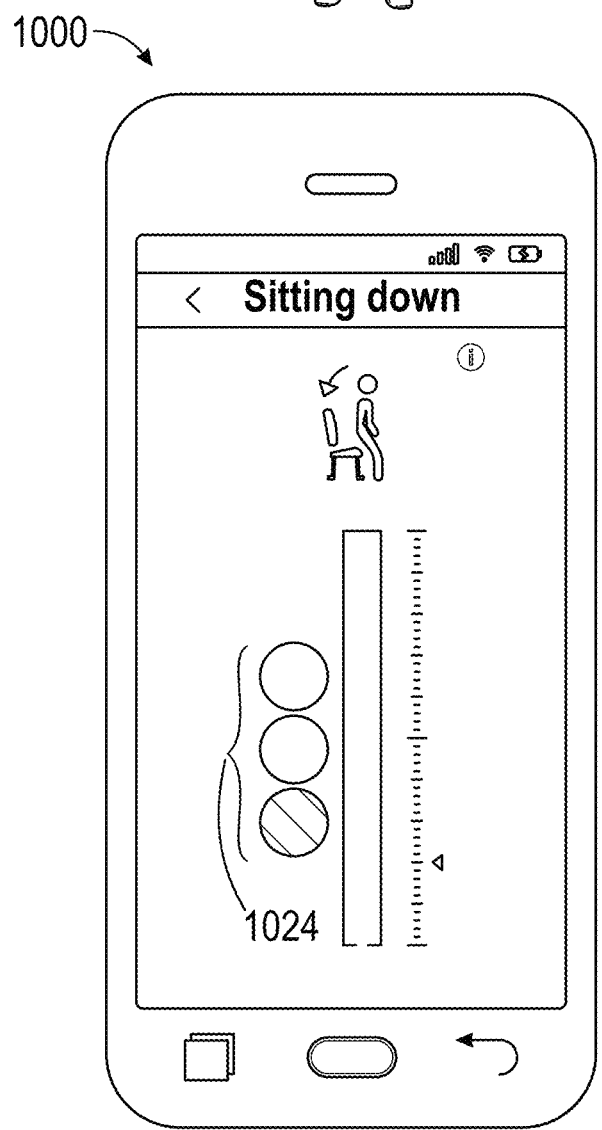
1000
FIG. 10A
FIG. 10B

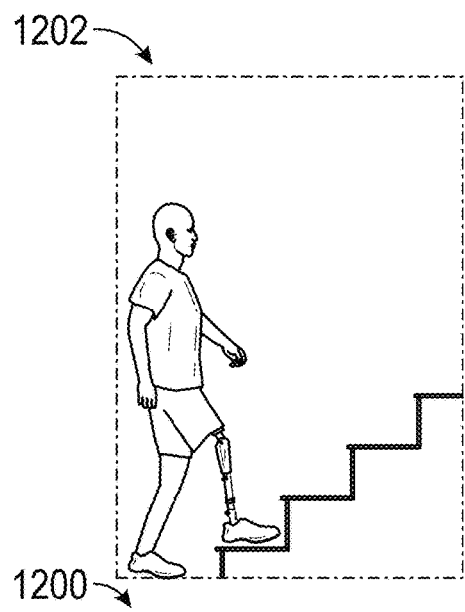
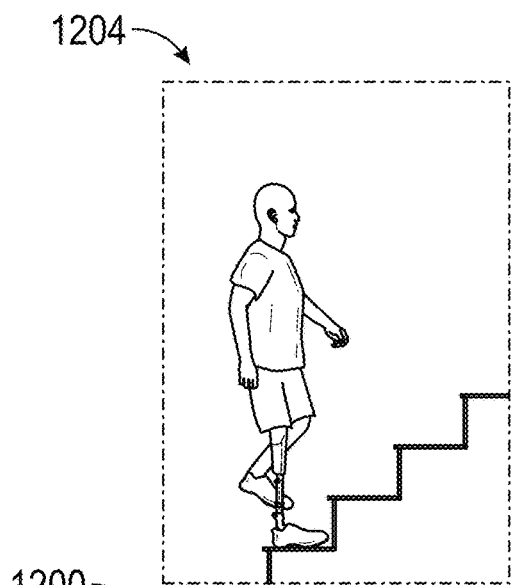
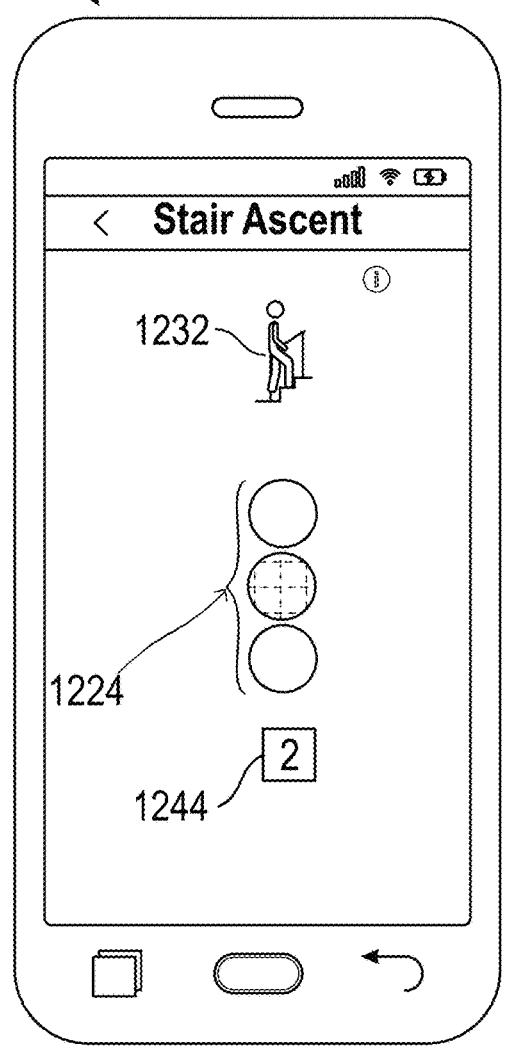
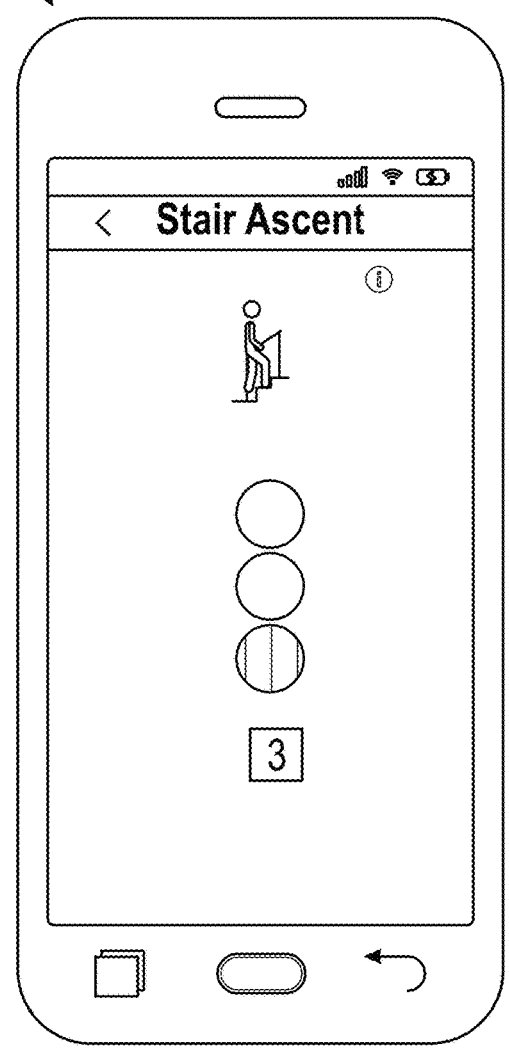
FIG. 12A    FIG. 12B

GRAPHICAL USER INTERFACE OF MOBILE DEVICE FOR IMPROVING INTERACTION WITH A PROSTHETIC OR ORTHOTIC DEVICE

TECHNICAL FIELD

The present application generally relates to a graphical user interface (GUI), and more particularly, a GUI for improving an interaction between a user and a prosthetic or orthotic device (POD).

BACKGROUND

Many kinds of prostheses have been devised to replace the missing limbs of amputees. In some cases, amputees compensate for a missing limb by relying more heavily on the sound limb. This over-reliance on the sound limb can increase the wear on the amputee's joints—leading to injury or pain.

SUMMARY

Various techniques for improving an interaction between a prosthetic and/or orthotic device (POD) and a user of the POD are described. In some cases, the POD can interact with a remote monitoring device that can generate in real time a graphical user interface (GUI) that includes various features, states, or information about the POD. By interacting with the POD in real-time and displaying the status or parameters of the POD in real time to a user, the GUI can improve various user-POD interactions including, but not limited to, weight bearing, rolling over the toe, sitting down, stair descent, and/or stair ascent. By improving the user-POD interactions, the GUI can prevent injuries and pain caused by user's incorrect use of the POD.

BRIEF DESCRIPTION OF THE DRAWINGS

FIGS. 9A-9B are diagrams illustrating embodiments of various states of a user-POD interaction for improving the user's skills to push-off onto the toes, and further illustrate a GUI of a monitoring device in communication with the POD.

FIGS. 10A-10D are diagrams illustrating embodiments of various states of a user-POD interaction for improving the user's symmetry while sitting down, and further illustrate a GUI of a monitoring device in communication with the POD.

FIGS. 12A-12C are diagrams illustrating embodiments of various states of a user-POD interaction for improving the user's symmetry while ascending stairs, and further illustrate a GUI of a monitoring device in communication with the POD.

DETAILED DESCRIPTION

Although certain embodiments and examples are described below, it will be understood that the disclosure extends beyond the specifically disclosed embodiments and/or uses and obvious modifications and equivalents thereof. Thus, it is intended that the scope of the disclosure herein disclosed should not be limited by any particular embodiments described below.

Good gait when interacting with a prosthetic or orthotic device (POD) is important to avoid long-term negative physiological impacts. However, even amputees that regularly meet with a physical therapist have difficulty achieving good gait because physical therapy inherently requires the physical therapist's subjective analysis and adjustments of the amputee's gait. That is, there nothing that quantifiably and objectively informs the amputee that he or she is correctly or incorrectly interacting with the POD.

Techniques for improving an interaction between a user and a POD (sometimes referred to as a user-POD interaction) are described. For example, a POD system can employ various sensors configured to measure various gait parameters including, but not limited to, an amount of load on the POD, a joint angle, a shank angle, or a braking power of the POD. By analyzing the sensor data and generating a graphical representation (for example, via a graphical user interface or GUI) of one or more gait parameters, the system can provide a visual quantification of good gait, thereby providing objective information to improve user-POD interaction. By improving the user-POD interactions, the system can prevent injuries and pain caused by user's incorrect use of the POD.

Overview of the Prosthetic or Orthotic Device (POD)

Figure 1:
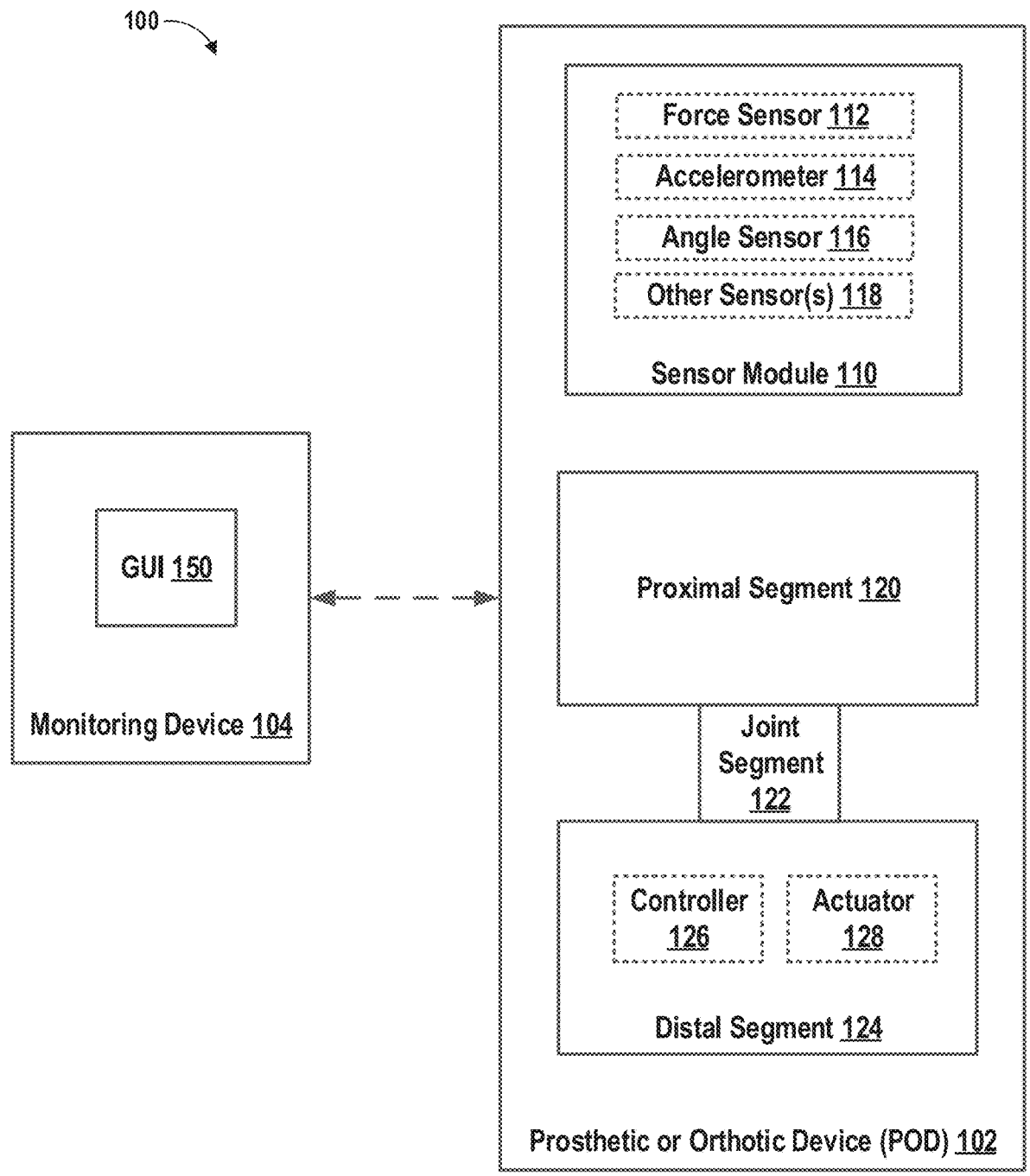
FIG. 1 illustrates a block diagram of a prosthetic and/or orthotic device (POD) having an electronically controlled prosthetic joint.

FIG. 1 illustrates a block diagram of a system 100 for improving interactions with a prosthetic or orthotic device (POD) 102. The system 100 includes a POD 102 having an electronically controlled prosthetic joint. The POD 102 includes a sensor module 110, a proximal segment 120, a joint segment 122, a distal segment 124, an actuator 128, and a controller 126. The system 100 also includes a monitoring device 104 configured to communicate with the POD 102 and display information via a graphical user interface (GUI) 150.

The proximal segment 120 of the POD 102 can include a socket to hold the stump of an above-knee, below-knee or other amputee. Furthermore, the proximal segment 120 can be connected to the distal segment 124 via the joint segment 122. The joint segment can be a knee joint, an ankle joint, hip joint, elbow joint, or the like. In some cases, the POD 102 can include both a knee joint and an ankle joint. The controller 126, actuator 128, and/or sensor module 110 can be located in any number of locations, including the proximal segment 120, the distal segment 124, or the joint segment 122. The actuator 128 can be implemented using a linear or rotary actuator; however, other types of actuators may be used without departing from the spirit and scope of the description.

The monitoring device 104 can communicate with the POD 102 and can be implemented as any of various computing devices including, but not limited to, a processor, a cell phone, smart phone, a tablet, a computer, a laptop, or the like. For example, the monitoring device 104 can receive gait parameter data from the POD 102. A software application residing on the monitoring device 104 can present at least some information associated with the gait parameter data via a GUI 150. In some cases, the gait parameter data can include sensor data, and, using the sensor data, the monitoring device can determine one or more of various gait parameters (for example, a ground interaction, a user weight, an amount of load placed on the POD, an amount of load placed on the sound limb, a weight distribution between the POD and sound limb, a shank angle, a joint angle, or a braking indicator) associated with the POD 102 over time. In addition or alternatively, the POD 102 (for example, the controller 126) can determine one or more of various gait parameters using the sensor data, and the gait parameter data received by the monitoring device 104 can include data indicative of the gait parameter determined by the POD 102. Any calculations and/or determinations described herein can be performed by any combination of the monitoring device 104, the POD 102, or another computing device. Accordingly, although some of the embodiments described herein may describe one or more determinations and/or calculations being performed by one of the monitoring device 104 or POD 102, it should be noted that, in some cases, each of the monitoring device 104 and POD 102 can perform all, none, or some of the calculations and/or determinations described herein.

The monitoring device 104 can communicate with the POD 102 wirelessly, for example, using Bluetooth, infrared, Wi-Fi, cellular, radio frequency (RF), or other wireless technology. In addition or alternatively, wired technologies may be used for communications.

Overview of the Sensor Module

The sensor module 110 of the POD 102 can capture information relating to load distribution, angles, orientation, braking, position, movement or other data of the POD 102. This information may be processed in real-time and communicated to the monitoring device 104, controller 126, or the like. The sensor module 110 can include one or more sensors including, but not limited to, a force sensor 112, and acceleration or orientation sensor 114 (for example, an accelerometer, a gyroscope, an orientation sensor, or a gravity sensor), an angle sensor 116, and/or one or more other sensors 118.

The force sensor 112 can provide force measurement data corresponding to an amount of load applied to the POD 102 by a user. For example, the force sensor 112 can be configured to measure a component of force applied to the POD 102 from the ground or other supporting surface in a direction substantially along or parallel to a shin longitudinal axis. In some cases, the force sensor 112 can be implemented as a load cell.

Force measurement data from the force sensor 112 can be used to determine various gait parameters associated with an interaction between the user and the POD, which can be referred to as a user-POD interaction. For example, using the force measurement data, the monitoring device 104 or POD 102 can determine whether the POD 102 is on or off the ground or other supporting surface.

In addition or alternatively, force measurement data can be used to determine an estimated weight of the user. For example, provided that a user delivers largely symmetric loading across the POD 102 and the sound limb, the weight of the user can be approximately equal to double the force measurement. Similarly, if the weight of the user is known or has been determined, the force measurement data can be used to determine a load placed on the POD 102, a load placed on the sound limb, or a weight distribution between the two. For example, the force measurement data can be used to determine whether a user is symmetrically loading the POD 102 and sound limb, or whether one of the POD 102 or sound limb is loaded more heavily. That is, a force measurement corresponding to less than half of the user's body weight can indicate that the user is more heavily loading the sound limb, while a force measurement corresponding to more than half of the user's body weight can indicate that the user is more heavily loading the POD. Accordingly, monitoring device 104 (or POD 102) can utilize the force measurement data from the force sensor 112 to determine how heavily the user is loading the POD 102 during any of the various user-POD interactions, as described herein.

In some cases, the force sensor 112 can include multiple force sensors, from which information regarding how the user distributes load across the POD 102 can be determined. For example, using force measurement data from a front force sensor configured to measure load on the front or toe end of the POD 102 and from a back force sensor configured to measure load on the rear or heel end of the POD 102, the monitoring device 104 (or POD 102) can determine the user's front/back load distribution. That is, a higher toe end load (as compared to the heel end load) can indicate that the user is leaning forward on his toes, while a higher heel end load (as compared to the toe end load) can indicate that the user is leaning backward on his heels. Similar determinations can be made if the force sensor 112 includes a right force sensor configured to measure load on the right side of the POD 102 and a left force sensor configured to measure load on the left side of the POD 102. That is, a higher right side load (as compared to the left side load) can indicate that the user is leaning to the right, while a higher left side load (as compared to the right side load) can indicate that the POD 102 is leaning to the left. In some cases, the system 100 can include any combination of one or more of a left side force sensor, a right side force sensor, a heel force sensor, a toe force sensor, or various other force sensors configured to measure at various locations of the POD 102.

The acceleration or orientation sensor 114 can provide acceleration data corresponding to acceleration of the POD 102 in one or more axes. For example, the acceleration or orientation sensor 114 can be configured to measure acceleration of the POD in multiple aces, such as two or three substantially mutually perpendicular axes. In addition or alternatively, the acceleration or orientation sensor 114 can be configured to measure an orientation of at least one of the proximal segment 120 or the distal segment 124. In some cases, the acceleration or orientation sensor 114 can be implemented as an accelerometer. In addition or alternatively, the sensor module 110 may include one or more other types of sensors in combination with, or in place of, accelerometers. For example, the sensor module 110 may include a gyroscope configured to measure the angular speed of body segments and/or the POD 102, an orientation sensor, or a gravity sensor.

The acceleration or orientation data from the from the acceleration or orientation sensor 114 can be used to determine various gait parameters associated with a user-POD interaction. For example, using the acceleration or orientation data, the monitoring device 104 or POD 102 can determine a shank angle, which can be described as an angle of the line of the shank (for example, corresponding to a shin of the user) relative to a line of the foot of the POD 102 or a walking surface. In some cases, the shank angle can be described in degrees. For example, the shank angle can be described in degrees of incline or recline from the vertical, measured in the sagittal plane. That is, an inclined shank angle can indicate that the POD 102 is leaning forward from the vertical, while a reclined shank angle can indicate that the POD is leaning backward from the vertical. Similarly, in some cases, the shank angle is described in degrees from the vertical. That is, a zero shank angle can indicate that the POD 102 is vertical; a positive shank angle can indicate that the POD 102 is leaning forward; and a negative shank angle can indicate that the POD 102 is leaning backward. Similar determinations can be made for directions other than forward and backward. For example, using the acceleration or orientation data, the monitoring device 104 can determine to what degree (if at all) the POD 102 is leaning in any direction, such as left, right, front, back, etc. Accordingly, the monitoring device 104 or POD 102 can utilize the acceleration or orientation data from the acceleration or orientation sensor 114 to determine whether the user is balanced or leaning during any of the various user-POD interactions, as described herein.

The angle sensor 116 can provide angle measurement data corresponding an angle between the proximal segment 120 and the distal segment 124. As a non-limiting example with respect to a prosthetic knee, proximal segment 120 can extend from the individual's thigh and the distal segment can correspond to the user's shank (for example, corresponding to a user's shin), and the angle sensor 116 can be configured to detect or measure a knee rotation angle (sometimes referred to as the knee angle or the joint angle). Accordingly, using angle measurement data from the angle sensor 116, the monitoring device 104 or POD 102 can determine the joint angle, and thus a degree to which the joint segment 122 is flexed or extended. For example, a 180 degree knee rotation angle can indicate that the POD 102 is straight (for example, the user's thigh and shank are parallel), while a 90 degree knee rotation angle can indicate that the POD is bent such that the user's shank is angled at 90 degrees relative to the user's thigh. Accordingly, the angle measurement data from the angle sensor 116 can be used determine whether the POD 102 is angled, and, in some cases, the degree to which the POD 102 is angled.

As another non-limiting example with respect to a prosthetic angle, the proximal segment 120 can extend from the user's shank and the distal segment 124 can correspond to the user's foot, and the angle sensor 116 can be configured to detect or measure an ankle rotation angle. Similarly, determinations can be made for a prosthetic hip, elbow, or the like.

Other suitable angle sensing devices may be utilized to determine the angle data. For example, in some cases, the angle sensor comprises a potentiometer. Power can be supplied to one end of the potentiometer while the other end is held at ground. In some cases, this can provide a signal output proportional to a position between 0° (for example, the POD 102 is completely bent) and 180° (for example, the POD 102 is straight). Other suitable angle sensing devices can include optical or magnetic shaft encoders or the like.

In some cases, the actuator 128 can be configured to provides resistive forces (sometimes referred to as resistive braking) to substantially simulate the position or motion of a natural knee joint during ambulation and/or other locomotory or stationary activities performed by a user. In other words, the actuator can act as a brake, varying its resistance to motion.

As a non-limiting example, the actuator 128 can be implemented as a rotary magnetorheological (MR) knee actuator that includes MR fluid. MR fluid is a field responsive (FR) fluid or medium that undergoes a rheology or viscosity change which is dependent on the magnitude of an applied magnetic field. This variation in fluid viscosity can control a magnitude of the shearing force/stress, torque or torsional resistance generated, and hence the level of damping provided by the knee actuator and/or the prosthetic knee.

Accordingly, the resistive braking effect of the POD 102 can be a function of the MR fluid viscosity, which in turn is a function of the magnetic field. In some cases, the controller 126 of the POD 102 passes a variable, controlled current through a coil, which creates the variable magnetic field. Thus, by controlling the current through the coil, the magnitude of this magnetic field is controlled, thereby controlling the POD's resistance to rotary motion.

In some cases, one or more other sensors 118 (for example, a current sensor) can be configured to measure the current flowing through the coil, or any other parameter relating to this resistive braking. Using this data and the relationships described above, the monitoring device 104 can determine various braking indicators related to the braking effect of the POD, including, but not limited to, resistance, the magnetic field, the fluid viscosity, the magnitude of the shearing force/stress, the torque or torsional resistance generated, or the level of damping.

Other suitable sensing devices may be utilized to determine one or more various parameters related to the braking effect of the POD 102. For example, in some cases, measurements from the force sensor 112 can be used by the controller 126 to determine or compute a component of torque applied to an actuator 128, which can, for example, adjust a braking torque applied by the actuator 128 to the POD 102. In some cases, the monitoring device 104 or POD 102 can similarly compute the component of torque applied to the actuator 128 using the force measurement data from the force sensor 112.

Example PODs

Figure 2:
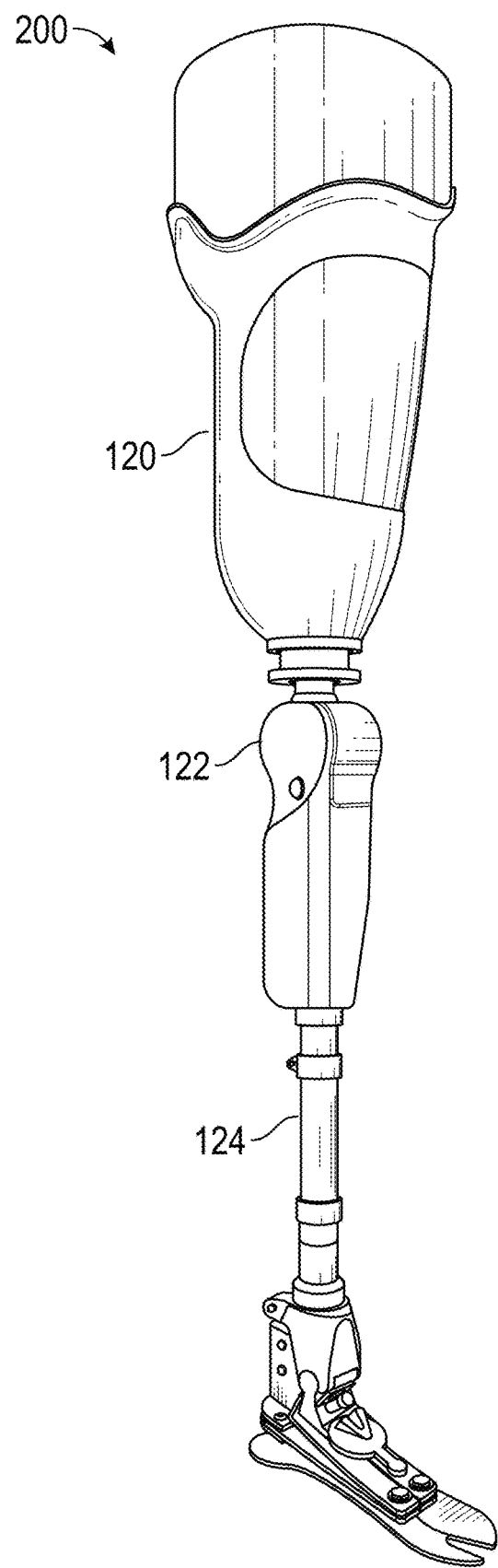
FIG. 2 illustrates an example knee POD, according to some embodiments.

FIG. 2 illustrates an example knee POD 200, according to some embodiments. As illustrated, the POD 200 comprises a proximal segment 120, a knee joint segment 122, and a distal segment 124. The proximal segment 120 includes a socket to hold the stump of an above-knee amputee. Furthermore, the proximal segment 120 is connected to the distal segment 124 via the joint segment 122.

Figure 3A:
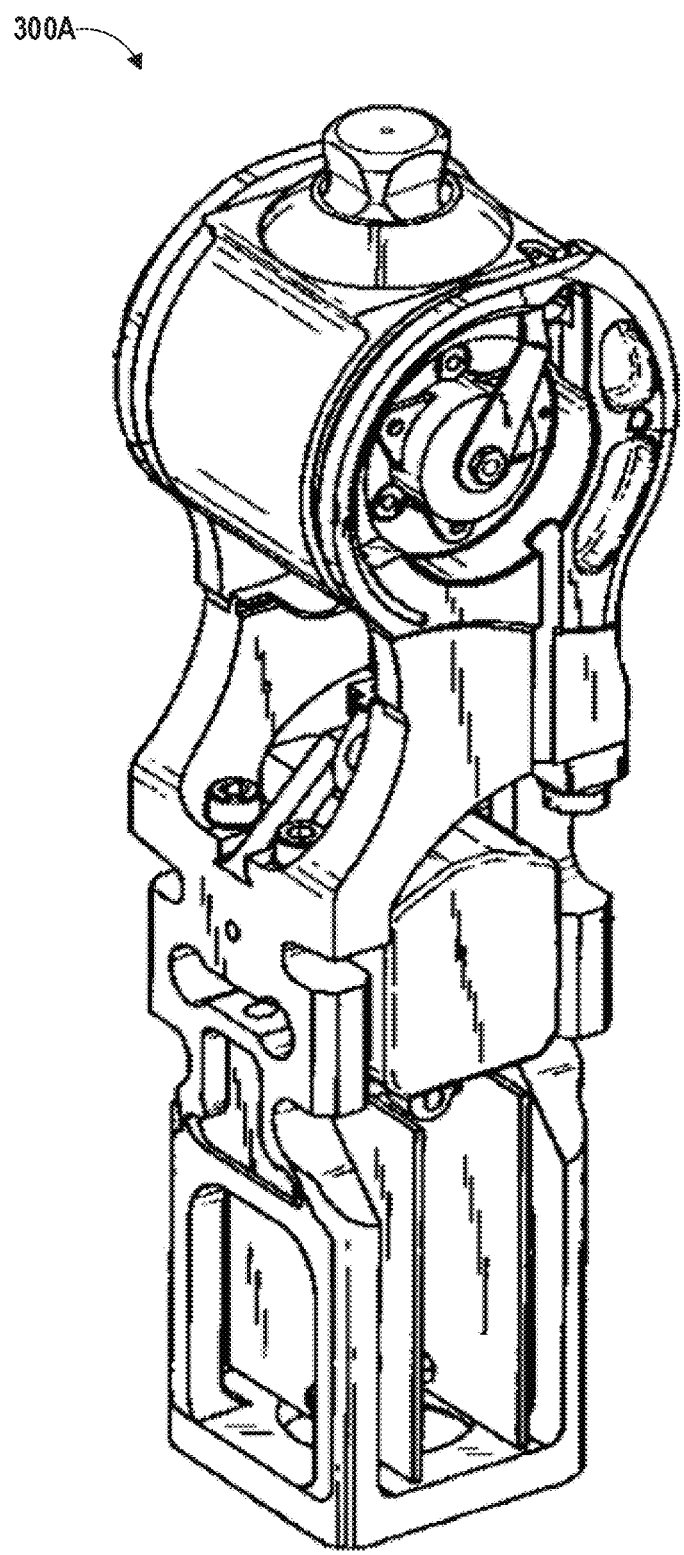
FIGS. 3A-3B illustrates diagrams of example knee PODs, according to some embodiments.

FIG. 3A illustrates an example prosthetic knee 300A, such as those described in greater detail in U.S. Pub. No. 2001/0029400, filed Jan. 22, 2001, entitled "ELECTRONICALLY CONTROLLED PROSTHETIC KNEE," U.S. Pub. No. 2005/0283257, filed Mar. 9, 2005, entitled "CONTROL SYSTEM AND METHOD FOR A PROSTHETIC KNEE," or U.S. Pub. No. 2006/0074493, filed May 6, 2005, entitled "SYSTEMS AND METHODS OF LOADING FLUID IN A PROSTHETIC KNEE," each of which is hereby incorporated by reference in its entirety and includes concepts that are compatible with and can be used in conjunction with any combination of the embodiments and/or features described herein.

Figure 3B:
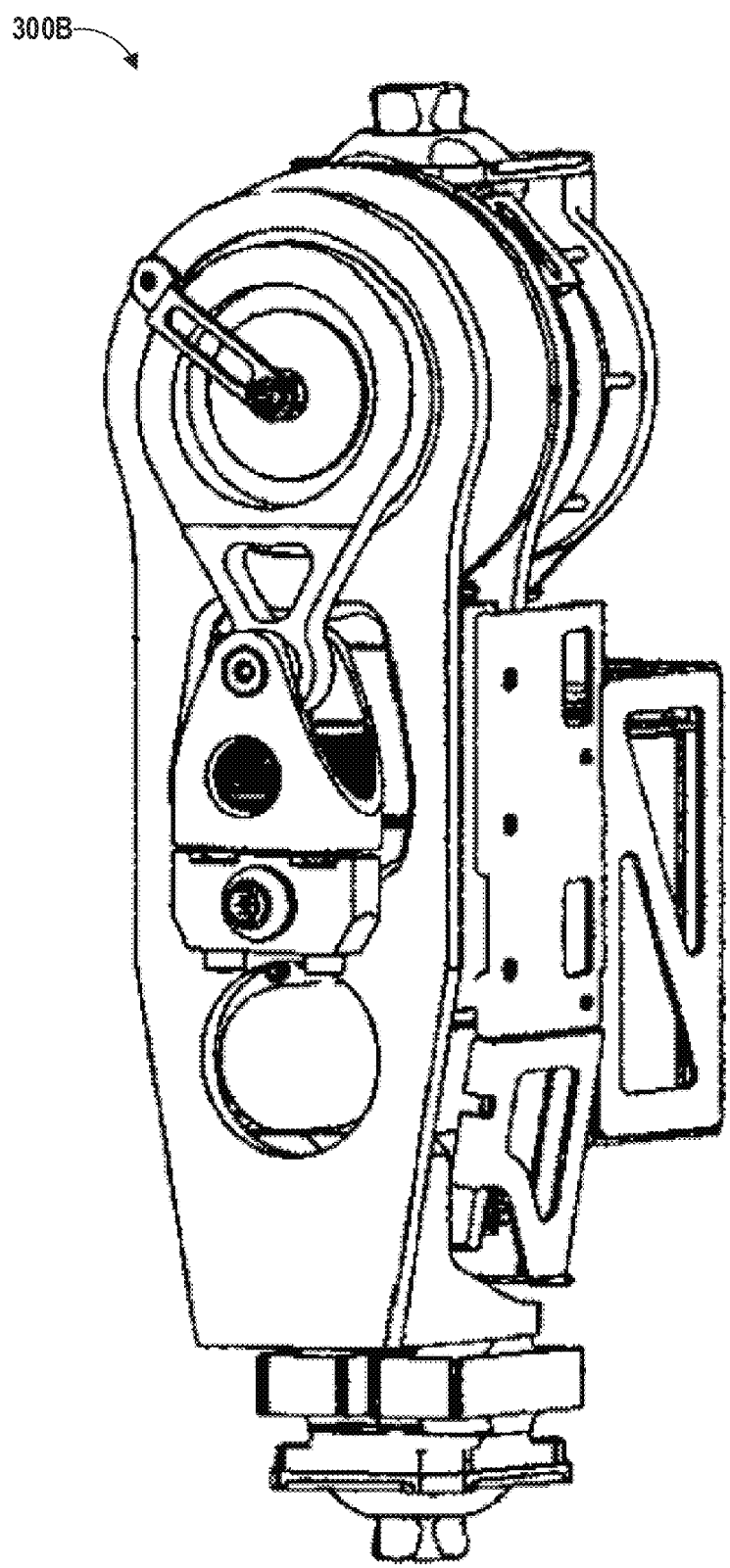

FIG. 3B illustrates an example motorized POD 300B, such as those described in greater detail in U.S. Pub. No. 2009/0299480, filed Jul. 7, 2009, entitled "JOINT ACTUATION MECHANISM FOR A PROSTHETIC AND/OR ORTHOTIC DEVICE HAVING A COMPLIANT TRANSMISSION," and U.S. Pun. No. 2011/0125290, filed Feb. 2, 2011, entitled "REACTIVE LAYER CONTROL SYSTEM FOR PROSTHETIC AND ORTHOTIC DEVICES," each of which is hereby incorporated by reference in its entirety and includes concepts that are compatible with and can be used in conjunction with any combination of the embodiments and/or features described herein.

Figure 4:
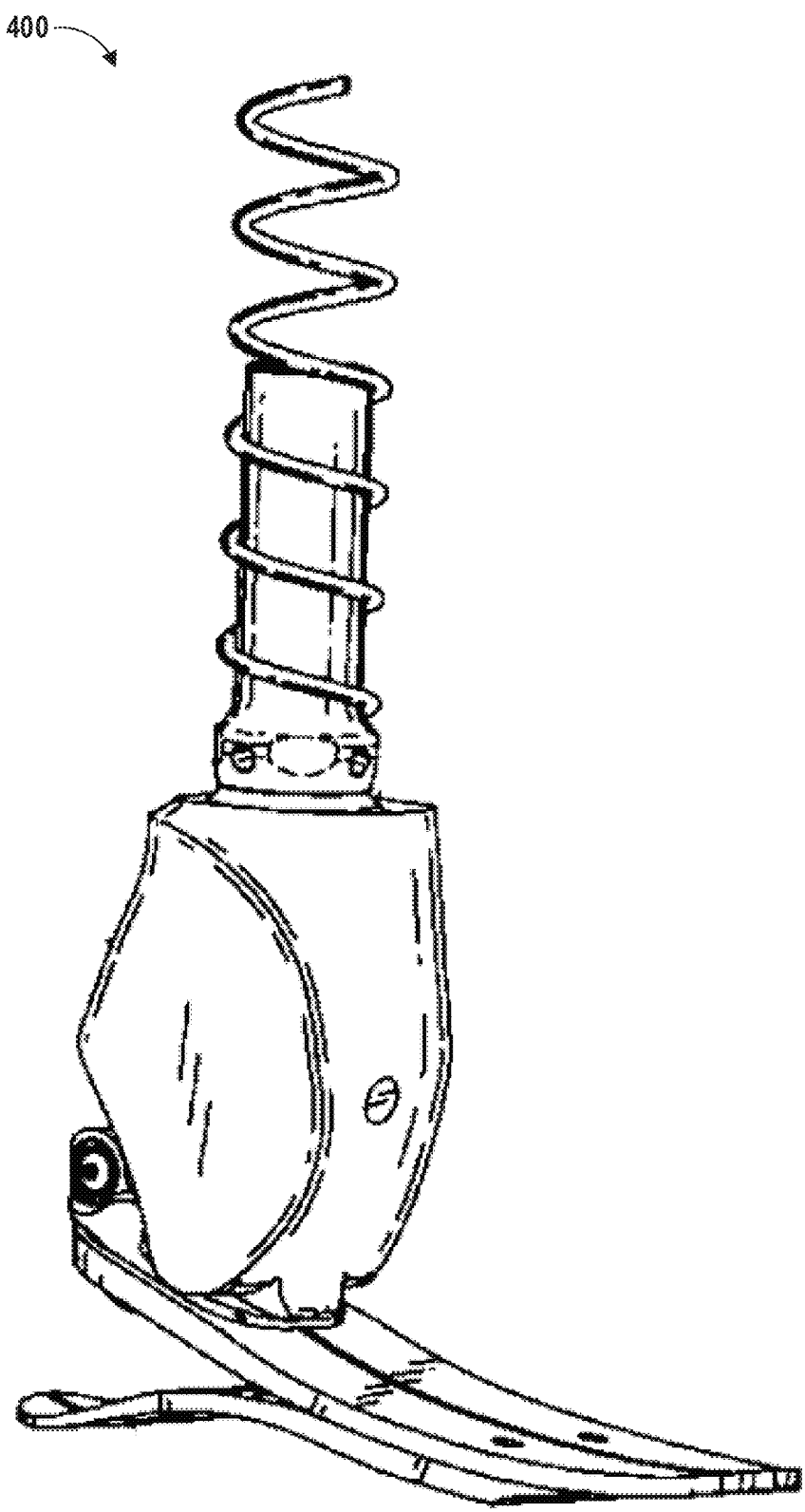
FIG. 4 illustrates an example ankle POD, according to some embodiments.

FIG. 4 illustrates an example ankle POD 400, such as those described in greater detail in U.S. Pub. No. 2011/0245931, filed Jun. 16, 2011, entitled "SYSTEMS AND METHODS FOR ACTUATING A PROSTHETIC ANKLE," which is hereby incorporated by reference in its entirety and includes concepts that are compatible with and can be used in conjunction with any combination of the embodiments and/or features described herein.

Graphical User Interface (GUI)

Figures 5, 6:
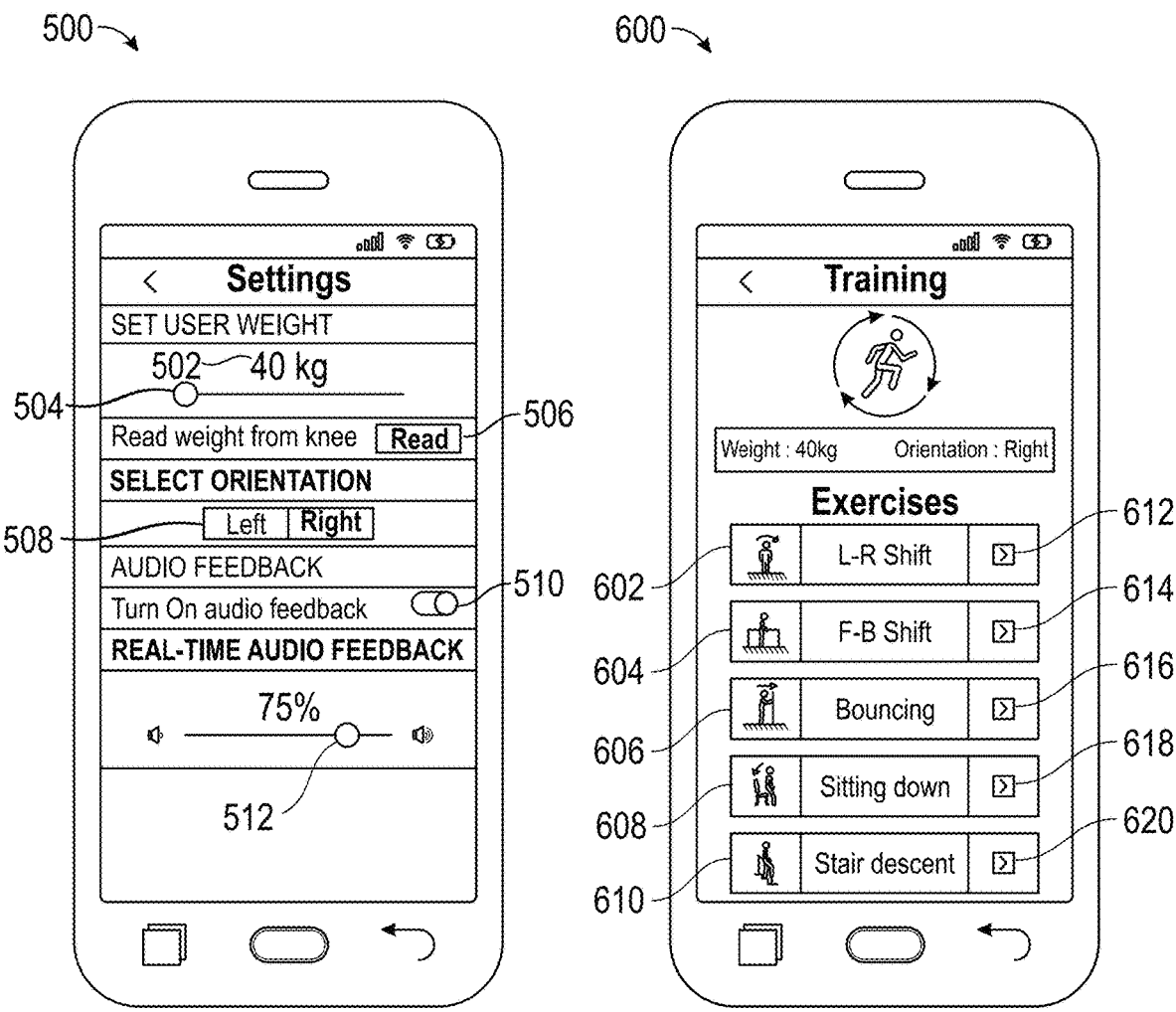
FIG. 5 illustrates an example graphical user interface (GUI) of a monitoring device, according to some embodiments.
FIG. 6 illustrates an example GUI displaying various display objects corresponding to user-POD interactions.

FIG. 5 illustrates an example graphical user interface (GUI) presented by a monitoring device (such as monitoring device 104 of FIG. 1), according to some embodiments. As illustrated, the GUI 500 includes various display objects that can be used to aid user-POD interactions. For example, the display objects include adjustable parameters including a POD orientation parameter 508 for selecting on which leg the user is wearing the POD 102, a user weight parameter 502 for inputting a user weight, an audio feedback parameter 510 for allowing or restricting audio feedback, and volume parameter 512 for adjusting a volume level of audible feedback.

The user weight parameter 502 can correspond to a weight (for example, in kilograms, pounds, or the like) of the user of the POD 102. The user weight parameter 502 can be a user input (non-limiting examples: via a keyboard or adjusted via a slidable scale 504). In addition or alternatively, as described herein, the monitoring device 104 or POD 102 can use force measurement data from a force sensor 112 to determine an estimated weight of the user. In some cases, the monitoring device 104 can make this determination automatically or in response to user input. For example, a user can initiate a weight determination procedure by selecting the "read" button 506.

Selecting a User-POD Interaction

FIG. 6 illustrates an example GUI 600 displaying various display objects corresponding to user-POD interactions. As shown, the display objects of the GUI 600 include a plurality of images 602, 604, 606, 608, 610 and selectable buttons 612, 614, 616, 618, 620 that are each associated with various user-POD interactions. In this example, the user-POD interactions, which are described in more detail below, include L-R shift, F-B shift, Bouncing, Sitting Down, and Stair Descent. However, it should be noted that fewer, more, or different user-POD interactions can be displayed on GUI 600. For example, the user-POD interactions can include Stair Ascent, as described herein with respect to FIGS. 12A-12C.

Lateral Weight Shifting

FIGS. 7A-7D are diagrams illustrating embodiments of various states of a user-POD interaction for improving the user's weight-bearing symmetry, and further illustrate a GUI 700 of a monitoring device (such as monitoring device 104 of FIG. 1) in communication with the POD 102. The GUI 700 includes various display objects that can be used to aid the user-POD interaction. In each of FIGS. 7A-7D, the display objects of the GUI 700 can be updated in real time and can reflect a corresponding state (for example, state 702, 704, 706, or 708) of the user-POD interaction.

As described herein, and with reference to FIG. 1, the system 100 includes a monitoring device 104 (for example, processor, cell phone, smart phone, tablet, computer, laptop, or the like) on which a software application can present a GUI (for example, GUI 600 of FIG. 6) that permits the user to select from various unique user-POD interactions. In this example, responsive to the user's selection of "L-R Shift," the application running on the monitoring device 104 presents GUI 700. L-R Shift (sometimes referred to as Left-Right Shift) can correspond to a user-POD interaction that develops lateral weight shifting and improves user's reliance on the POD by increasing or decreasing the amount of weight the user places on the POD 102, thereby improving the user's gait. As described herein, the monitoring device 104 can communicate with the POD 102 to obtain gait parameter data. In this example, the gait parameter data can correspond to data from one or more force sensors 112, among other sensors.

In the illustrated embodiment of FIGS. 7A-7D, the GUI 700 includes various display objects such as a graphical indication 720 representing an amount of load placed on the POD 102, a timing indicator 734, a stick figure representation 732 of the selected user-POD interaction (in this case, L-R Shift), a success indicator 736 (for example, illustrated in FIG. 7D), a weight/load threshold marker 728, and a repetition threshold 726, 727. The various display objects can be used to aid the user in improving the user-POD interaction. In some cases, the GUI 700 can include fewer, more or different display objects, as desired.

The graphical indication 720 can be indicative of an amount of load placed on the POD 102, an amount of load placed on a sound limb of a user fitted with the POD 102, or a load distribution between the POD and the sound limb. For example, the graphical indication 720 can include shaded regions 740, 742, which can represent a load of the user. That is, the first shaded region 740 can represent an amount of load place on the POD 102 and the second shaded region 742 can represent an amount of load placed on the sound limb. A relative size of the shaded regions 740, 742 can indicate a distribution of load. For example, a larger shaded region (as compared to the other shaded region) can indicate that the user is loading that leg more heavily than the other leg. Alternatively, in some cases, a smaller shaded region (as compared to the other shaded region) can indicate that the user is loading that leg more heavily than the other leg.

In the illustrated embodiments, the graphical indication 720 is a bar display including two vertical bars: a vertical bar 722 corresponding to load placed on the individual's right leg (the prosthetic leg in this example) and the vertical bar 724 can correspond to load placed on the individual's left leg (the sound limb in this example). However, in various embodiments, the vertical bars 722, 724 can correspond to either leg. For example, the vertical bar 722 can correspond to a user's left leg. It will be understood that the loading and/or weight distribution of the POD, the sound limb, or both can be presented in various ways. For example, fewer, more, or different display objects can be utilized to represent a load of the user. In some cases, only an amount of load on the POD is indicated by the GUI 700.

The timing indicator 734 can provide a representation of a period over which the user is to maintain a weight/load threshold in order to complete a successful repetition of the user-POD interaction. In some cases, the weight/load threshold indicates an absolute minimum load needed to satisfy the weight/load threshold and complete a successful repetition of the user-POD interaction. For example, the load/weight distribution threshold can be represented by a weight/load threshold marker 728 that indicates a level of shading that the shaded regions 740 or 742 should meet in order to satisfy the weight/load threshold. That is, the weight/load threshold marker 728 can indicate an amount of load on the POD 102 or sound limb needed to complete a successful repetition of the user-POD interaction.

In some cases, the weight/load threshold is not absolute or the weight/load threshold marker 728 does not indicate an absolute load or shading to complete a successful repetition of the user-POD interaction. Rather, in some cases, the weight/load threshold can be satisfied if a load of the POD 102 or sound limb falls within a range of loads. These ranges can be referred to as weight thresholds. Accordingly, if the load on the POD or the sound limb is within a weight threshold of the weight/load threshold marker 728, the weight/load threshold can be satisfied. The weight threshold can correspond to an acceptable percentage. For example, while the weight/load threshold marker 728 may be set at 50/50 (for example, 50% weight on the POD and 50% weight on the sound limb), the weight threshold may allow for an addition margin to satisfy the weight/load threshold. For example, the weight threshold can provide an additional buffer of +/−2% (48/52), +/−4% (46/54), +/−6% (44/56), +/−8% (42/58), or +/−10% (40/60) to the weight/load threshold from the marker 728. In some cases, the weight threshold, the weight/load threshold, or the weight/load threshold marker 728 are adjustable parameters such that the user can adjust requirements to satisfy the weight/load threshold. For example, to increase a complexity of the user-POD interaction, the weight/load threshold can be adjusted to require additional loading of the POD 102.

In some cases, the display 720 can include additional indicators that reflect whether the weight/load threshold is satisfied. For example, the color of the shaded regions 740, 742 can represent whether the weight/load threshold is satisfied. That is, a first color (for example, orange) can indicate that the load placed on the POD 102 and/or the sound limb do not satisfy the weight/load threshold. In contrast, a second color (for example, green) can indicate that the load placed on the POD 102 and/or the sound limb do satisfy the weight/load threshold.

In the illustrated embodiment, the timing indicator 734 is shown as a pie countdown timer that starts out filled and slowly disappears as a timer runs down. The pie countdown timer can start when the user transfers enough weight (for example, as indicated by the weight/load threshold) to the POD 102. It will be understood that the timing indicator 734 can be implemented in a variety of ways. For example, the timing indicator can display a number and count down (or up) the amount to satisfy the period over which the user is to maintain the threshold load.

Figures 7A, 7B:
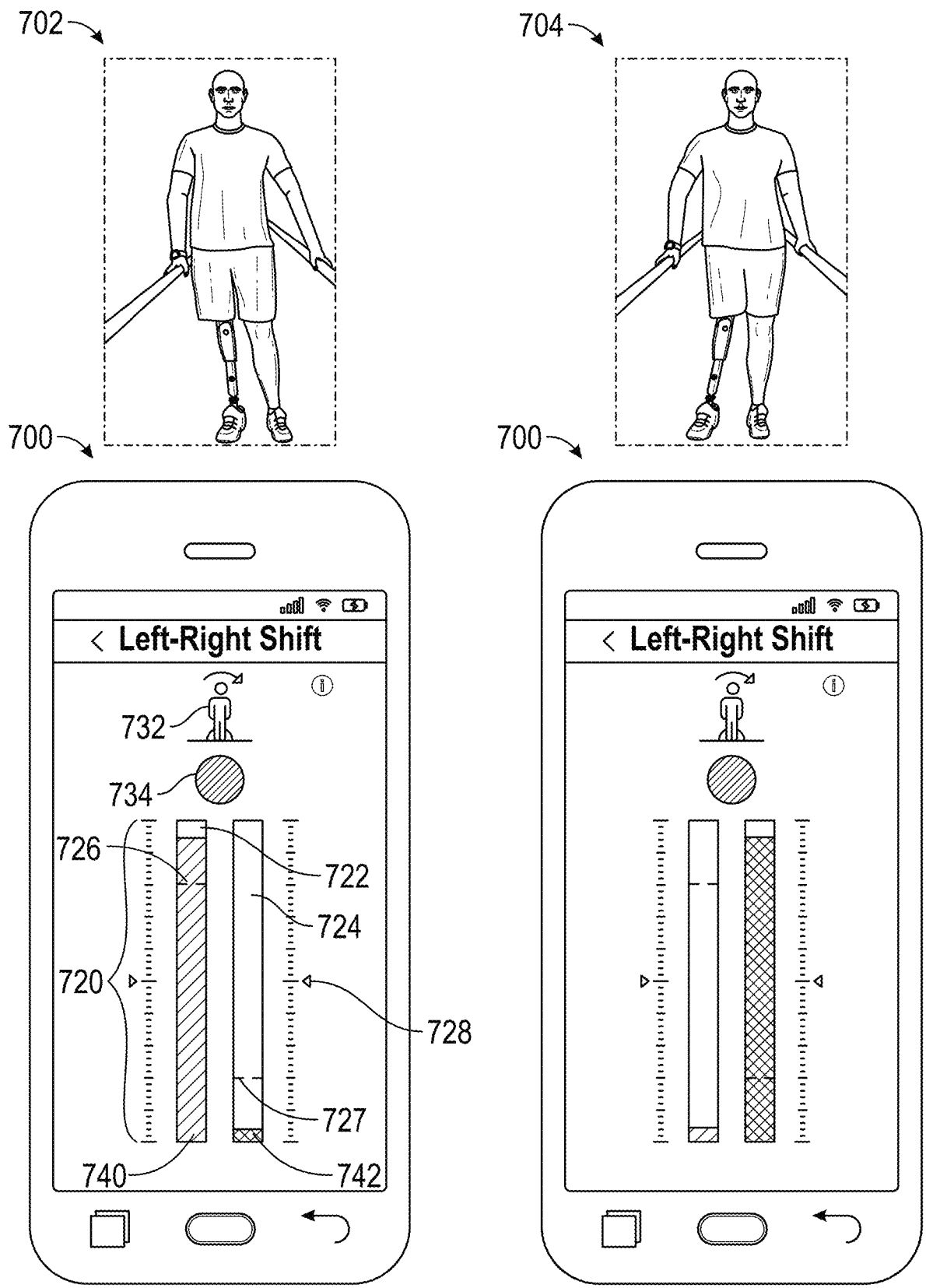
FIGS. 7A-7D are diagrams illustrating embodiments of various states of a user-POD interaction for improving the user's weight-bearing symmetry, and further illustrate a GUI of a monitoring device in communication with the POD.
Figure 7C:
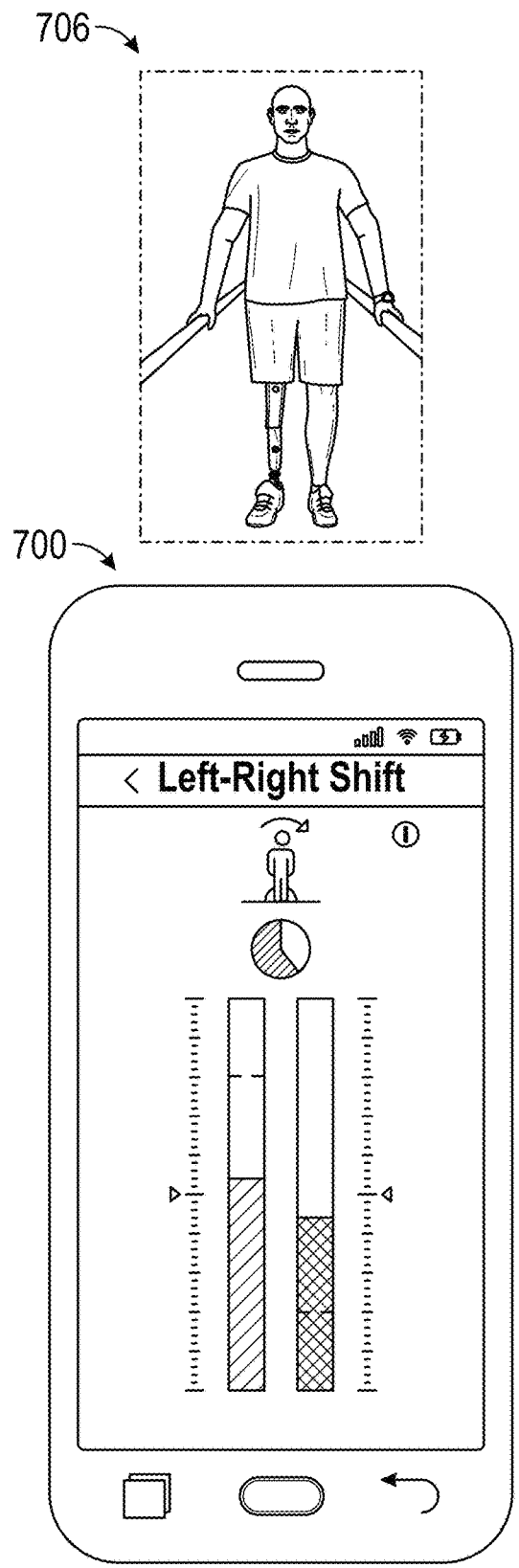
Figure 7D:
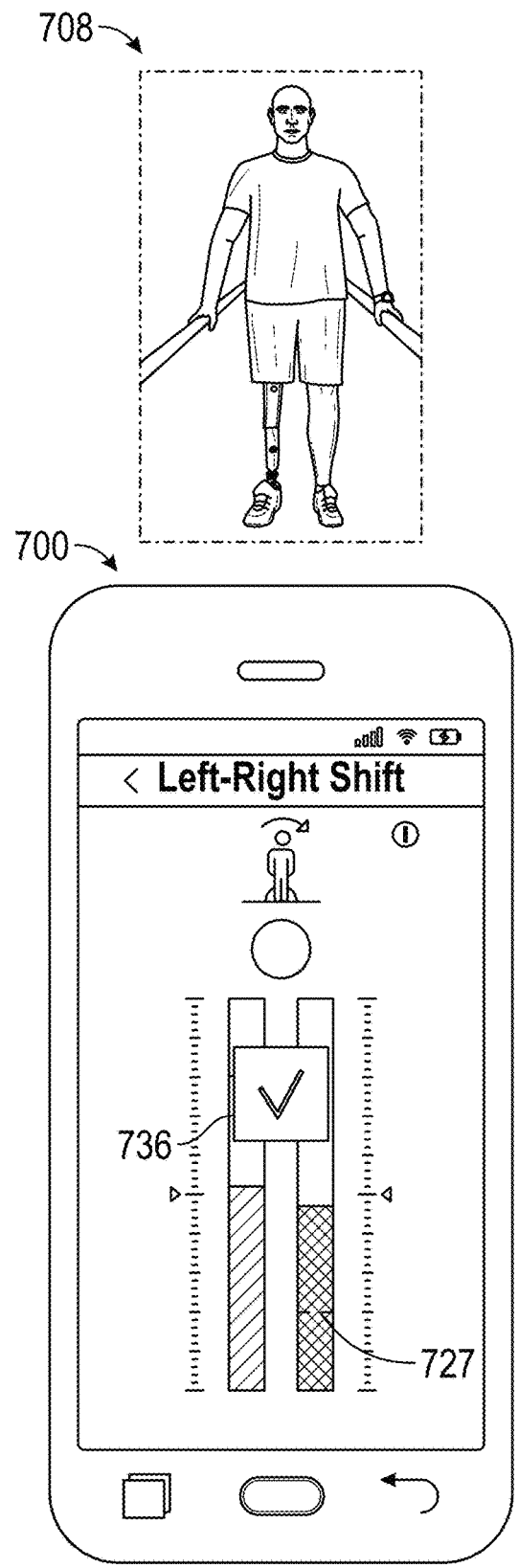

In some cases, as illustrated in FIG. 7D, the GUI 700 will provide a success indicator 736 (indicative of a successful repetition) if the weight/load threshold is held for a period of time (for example, 3, 5, or 10 seconds). In response to a determination that the load passes a repetition threshold 726 or 727, the GUI 700 can proceed to a next repetition of the user-POD interaction. In the illustrated embodiment of FIG. 7D, the repetition threshold 727 corresponds to an amount of load to be added to the POD 102 and/or an amount of load to be removed from the sound limb. In other words, to satisfy the repetition threshold 727 of FIG. 7D (and proceed to the next repetition), the monitoring device 104 or POD 102 can determine that the user shifted his weight on the POD 102 such that the shaded region 740 passes (for example, moves above) threshold 726 or can determine that the user shifted his weight off of the sound limb such that shaded region 742 passes (for example, below) threshold 727. However, in some cases, the repetition thresholds 726, 727 can correspond to an amount of load to be removed from the POD 102 and/or an amount of load to be added to the sound limb.

In response to the user increasing or decreasing the load on the POD 102, the monitoring device 104 or the POD 102 can detect the shift and communicate the load information to the monitoring device 104. The monitoring device 104, in turn, can update the display in real-time with the weight distribution of the user on the GUI 700. For example, as illustrated in image 702, the user can lean to the right so as to increase loading on POD 102. When the user shifts his weight onto the POD 102, the shaded region 740 of the first vertical bar 722 of the GUI 700 increases to represent added load on the POD 102. Furthermore, the shaded region 742 of the second vertical bar 724 decreases to indicate a reduced load on the sound limb.

As illustrated in FIG. 7B, in response to the user shifting his weight from the POD 102 to the sound limb (for example, as illustrated in image 704), the monitoring device 104 or the POD 102 can detect the decreased load and the monitoring device 104 can update the GUI 700 in real-time. For example, as illustrated in image 704, the user can lean to the left so as to increase loading on his sound limb. In response to the user shifting his weight onto the sound limb, the shaded region 740 of the first vertical bar 722 of the GUI 700 decreases in size to represent reduced load on the POD 102, and the shaded region 742 of the second vertical bar 724 increases in size to indicate the increased load on the sound limb.

As illustrated in FIG. 7C, in response to the user shifting his weight to a neutral position (for example, as illustrated in image 706), which may also be referred to as equal load-bearing or equal weight-bearing and can correspond to a relatively equal weight balance on each foot, the monitoring device 104 can update the GUI 700 in real-time.

Based on the gait parameter data received from the POD 102, the monitoring device 104 can visually indicate that the weight distribution of the user satisfies the weight/load threshold. Once the weight/load threshold is satisfied, the POD 102 of the monitoring device 104 can monitor the amount of time that the weight/load threshold is maintained. In the illustrated embodiment, once the weight/load threshold is satisfied, the monitoring device 104 displays a timer and further displays the amount of time that the user has maintained the weight/load threshold using the timing indicator 734. For example, once the weight/load threshold is satisfied, the timing indicator 734 begins countdown, as illustrated in FIG. 7C.

As illustrated in FIG. 7D, the monitoring device 104 or POD 102 can monitor the POD 102 over the time period. Based on a determination that the weight/load threshold is satisfied over the time period, the monitoring device 104 can cause display on the GUI 700 of a success indicator 736, indicating that the weight/load threshold was satisfied for the time period. The user can lean to the right so as to increase loading on his prosthetic leg. In some cases, based on a determination that the repetition threshold 726 or 727 is satisfied, the monitoring device 104 indicate that the user has initiated the next repetition. The user can repeat the user-POD interaction until a desired number of repetitions have been completed. Each of states 702, 704, 706, and 708 illustrate a user holding on to a handrail. However, it will be understood that the handrail can be removed.

By interacting with the POD 102 and displaying the status or parameters of the POD 102 in real time to the user, the monitoring device 104 can improve the user-POD interaction. By improving the user-POD interaction, the monitoring device 104 can prevent injuries and pain caused by user's incorrect use of the POD 102.

Forward and Backward Weight Shifting and Rolling Over the Toe

FIGS. 8A-8D are diagrams illustrating embodiments of various states of a user-POD interaction for improving the user's skills to roll-over the toe, and further illustrate a GUI 800 of a monitoring device (such as monitoring device 104 of FIG. 1) in communication with the POD. The GUI 800 includes various display objects that can be used to aid the user-POD interaction. In each of FIGS. 8A-8D, the display objects of the GUI 800 can be updated in real time and can reflect a corresponding state (for example, state 802, 804, 806, or 808) of the user-POD interaction.

As described herein, a software application on the monitoring device 104 can present a GUI (for example, GUI 600 of FIG. 6) that permits the user to select from various unique user-POD interactions. In this example, responsive to the user's selection of "F-B shift," the application running on the monitoring device 104 presents GUI 800. F-B shift (sometimes referred to as Forwards-Backwards Shift) corresponds to a user-POD interaction that develops skills to rollover the toe and improves user's reliance on the POD by improving the user's balance and orientation when the user shifts forward or backward. As described herein, the monitoring device 104 can communicate with the POD 102 to obtain gait parameter data. In this example, the gait parameter data can correspond to data from a force sensor 112 and an acceleration or orientation sensor 114, among other sensors.

In the illustrated embodiment of FIGS. 8A-8D, the GUI 800 includes various display objects such as a graphical indication 820, a stick figure representation 832 of the selected user-POD interaction (in this case, the F-B shift), and/or a success indicator 836. The graphical indication 820 can include a load indicator 824 and/or an orientation indicator 822. The various indicators, or display objects, can be used to aid the user in improving the user-POD interaction. In some cases, the GUI 800 can include fewer, more, or different display objects, as desired.

The load indicator 824 can be indicative of an amount of load placed on the POD 102, the sound limb, or an inter-foot distribution between the POD 102 and the sound limb. For example, the load indicator 824 can be shaded, colored, or otherwise configured to represent a load of the POD 102. That is, a first color (for example, red or yellow) can indicate that the load or weight distribution does not satisfy a weight/load threshold (for example, as described herein with respect to FIGS. 7A-7D), while a second color (for example, green) can indicate that the load or weight distribution satisfies the weight/load threshold. In addition or alternatively, multiple colors can be used to indicate intra-foot weight distribution of the POD. For example, darker colors can indicate higher load, while lighter colors can indicate lower load.

In the illustrated embodiment, the load indicator 824 is shown as a representation of a footprint 824 that can be shaded, colored, or otherwise configured to represent a load of the POD and/or the user's inter-foot weight distribution (for example, a weight distribution between the POD and sound limb). However, it will be understood that the load indicator 824 can be implemented in a variety of ways.

The orientation indicator 822 can represent a shank angle or one or more various orientation or weight distribution characteristics. For example, the orientation indicator 822 can represent the user's intra-foot weight distribution, such as a vertical weight distribution (for example, from toe to heel) or horizontal weight distribution (for example, from left to right).

In the illustrated embodiments, the orientation indicator 822 is shown as a horizontal dashed line 802 that can represent one or more of various orientation or weight distribution characteristics. For example, the orientation indicator 822 can be located toward the front or top of the footprint 804 if the shank angle is inclined (for example, if the shank is leaning forward from the vertical, also known as on the toes), and the orientation indicator 822 can be located toward the back or bottom of the footprint 804 if the shank angle is reclined (for example, if the shank is leaning backward from the vertical, as known as on the heels).

As another example, the orientation indicator 822 can indicate a center of pressure of the POD 102. For example, the orientation indicator 822 can be located near the front (or top) of the footprint 804 to indicate center of pressure near the toe of the POD 102. Similarly, the orientation indicator 822 can be located near the back (or bottom) of the footprint 804 to indicate center of pressure near the heel of the POD. It will be understood that the orientation indicator 804 can be implemented in a variety of ways.

Figures 8A, 8B:
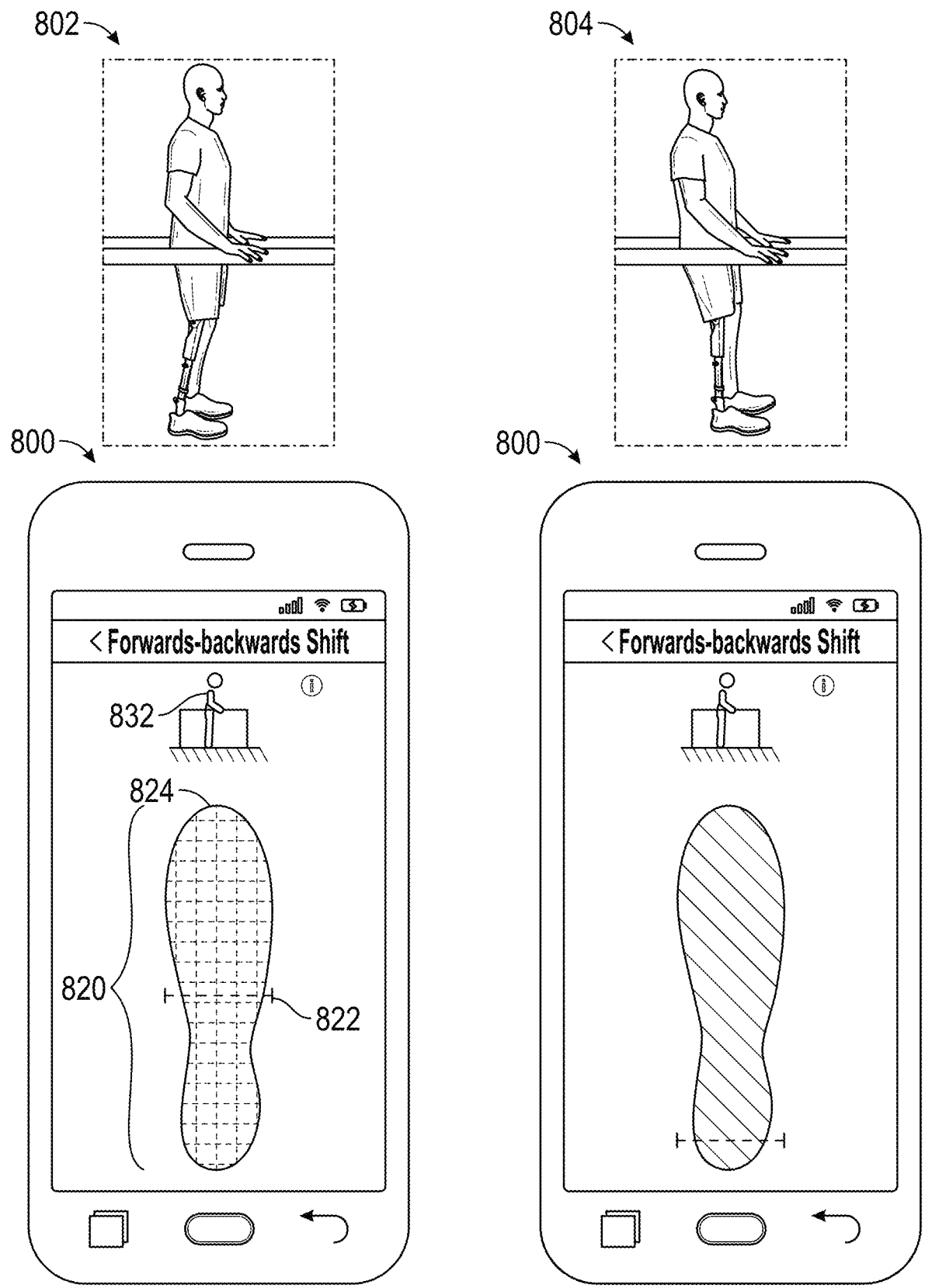
FIGS. 8A-8D are diagrams illustrating embodiments of various states of a user-POD interaction for improving the user's skills to roll-over the toe, and further illustrate a GUI of a monitoring device in communication with the POD.
Figures 8C, 8D:
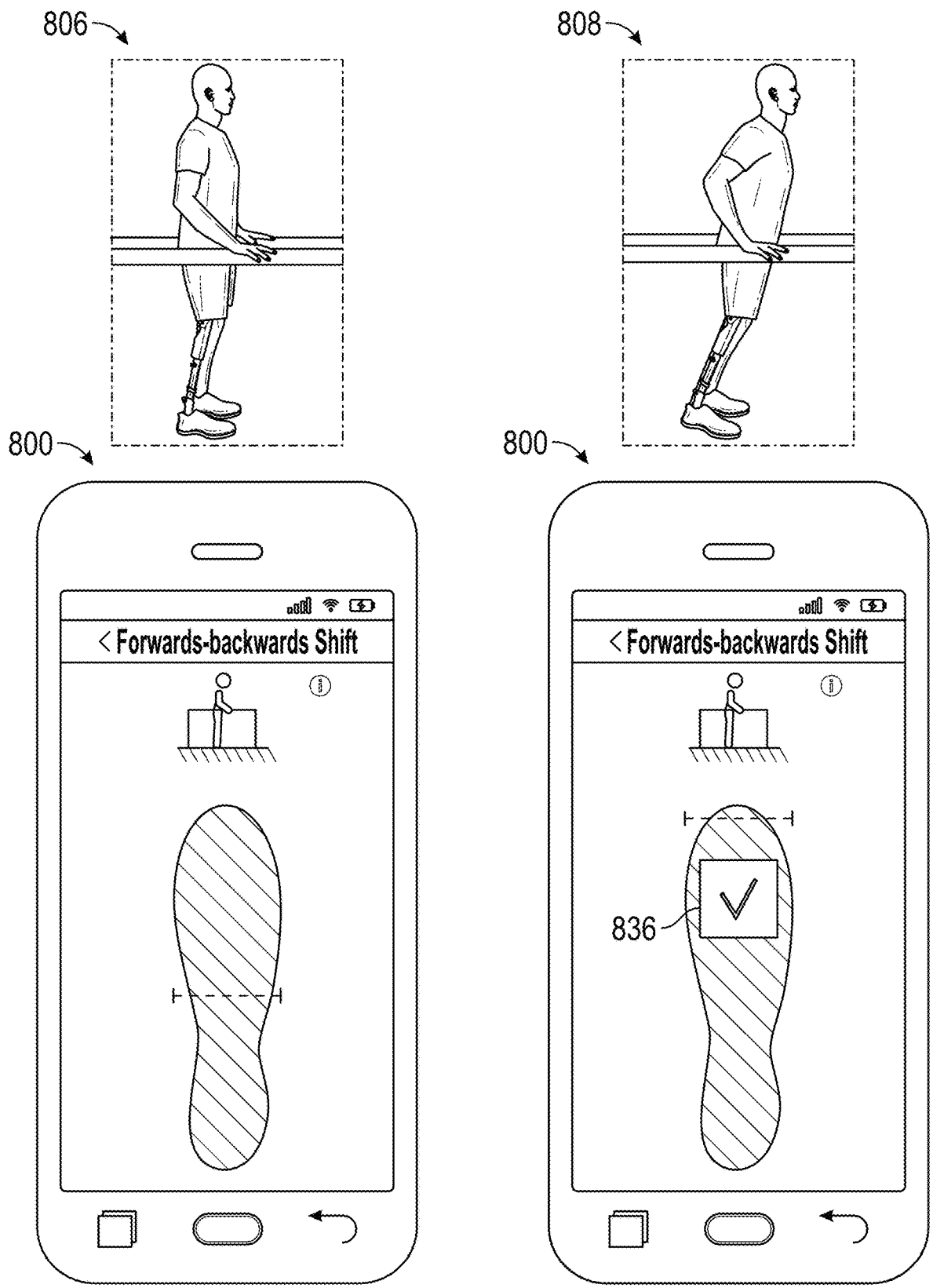

In some cases, as illustrated in FIG. 8D, the GUI 800 will provide a success indicator 836 (for example, indicative a successful repetition) if the user loads the POD and sound side while successfully transitioning from loading of the heel to loading of the toe (or vice versa). It will be understood that the success indicator 836 can be implemented in a variety of ways. For example, the success indicator 836 can display a number of successful repetitions or can display words of encouragement to the user, such as "Good Job," "Completed," or the like. Furthermore, in some cases, the GUI 800 can display instructions to the user, such as "shift weight to toes" or "shift weight to heels." However, it will be understood that any of various instructions could be presented to the user to further improve the user-POD interaction.

In response to the user increasing or decreasing the load on the POD 102, the POD 102 or monitoring device 104 can detect the shift. In response, the monitoring device 104, can update the display in real-time with the intra-foot or inter-foot weight distribution of the user on the GUI 800. In some cases, color or shading of the load distribution indicator 824 can indicate whether the user's weight is distributed evenly. Alternatively, the load distribution indicator 824 can indicate whether the user is properly loading the POD 102. For example, as illustrated in FIG. 8A, a first color (for example, yellow) or shading can indicate insufficient loading of the POD 102. In some cases, when the POD is not sufficiently loaded (for example, when the weight distribution is not approximately equal), the monitoring device 104 does not permit movement of the orientation indicator 822. Thus, the monitoring device 104 can require that the user correct his weight distribution (for example, satisfy a weight/load threshold) before the monitoring device 104 permits the user to proceed with completing a successful user-POD interaction.

In response to the user inclining (for example, shifting his weight forward onto his toes) or reclining (for example, shifting his weight backward onto his heels), the POD 102 or monitoring device 104 can detect the shift. In response, the monitoring device 104, can update the display in real-time with information regarding the inter-foot (for example, POD) weight distribution or the shank angle of the user on the GUI 800. In some cases, the location of the orientation indicator 822 can indicate to what degree the user is leaning forward, leaning backward, leaning sideways, or the like. Accordingly, when the user leans forward so as to increase loading on his toes, the orientation indicator 822 can move forward or up the footprint 804. Similarly, when the user leans backward so as to increase loading on his heels, the orientation indicator 822 can move backward or down the footprint 804.

For example, as illustrated in image 802, in response to a determination that the inter-foot weight distribution or the POD load does not satisfy a threshold, the monitoring device 104 can update the load distribution indicator 824 of the GUI 800 in real-time to indicate (for example, via a first color or shading) that the user is not sufficiently loading the POD 102. Furthermore, the monitoring device 104 can disregard any intra-foot or orientation data until the user's inter-foot weight distribution satisfies the threshold.

As illustrated in FIG. 8B, in response to the user shifting his weight across both legs to a neutral position, which can correspond to a relatively equal weight balance on each foot, the POD 102 or the monitoring device 104 can detect the load change, and the monitoring device 104 can update the load distribution indicator 824 of the GUI 800 in real-time to indicate (for example, via a second color or shading) that the user is sufficiently loading the POD.

Further, in response to the user shifting his weight backward (for example, as illustrated in image 804), the POD 102 or the monitoring device 104 can detect the shift in weight or change in shank angle, and the monitoring device 104 can update the GUI 800 in real-time. For example, in response to the user shifting his weight onto his heels, the GUI 800 can display the orientation indicator 804 at the back or bottom of the footprint 804.

As illustrated in FIG. 8C, in response to the user retaining relatively equal weight balance on each foot and adjust the shank angle to correspond to vertical (for example, as illustrated in image 806), the monitoring device 104 can update the GUI 800 in real-time.

As illustrated in FIG. 8D, the monitoring device 104 or the POD 102 can monitor the POD 102 over the time period. Based on a determination that the weight distribution threshold (for example, relatively equal weight balance on each foot) is satisfied over the time period, and a determination that the user shifted his weight from backward (for example, as illustrated in image 804) to forward (for example, as illustrated in image 808), the monitoring device 104 can cause on the GUI 800 of a success indicator 836, indicating that the user completed a successful repetition of the user-POD interaction. Similarly, in some cases, the monitoring device 104 can cause on the GUI 800 of a success indicator 836 if the user successfully shifts his weight from forward to backward. The user can repeat the user-POD interaction until a desired number of repetitions have been completed. Although each of states 802, 804, 806, and 808 illustrate a user holding on to a handrail, it will be understood that in some cases the handrail is unnecessary, or may be used for balancing purposes.

By interacting with the POD 102 in real-time and displaying the status or parameters of the POD 102 in real time to the user, the monitoring device 104 can improve the user-POD interaction. By improving the user-POD interaction, the system can prevent injuries and pain caused by user's incorrect use of the POD.

Push-Off

FIGS. 9A-9B are diagrams illustrating embodiments of various states of a user-POD interaction for improving the user's skills to push-off onto the toes, and further illustrate a GUI of a monitoring device (such as monitoring device 104 of FIG. 1) in communication with the POD. The GUI 900 includes various display objects that can be used to aid the user-POD interaction. In each of FIGS. 9A-9B, the display objects of the GUI 900 can be updated in real time and can reflect a corresponding state (for example, state 902, or 904) of the user-POD interaction.

As described herein, a software application on the monitoring device 104 can present a GUI (for example, GUI 600 of FIG. 6) that permits the user to select from various unique user-POD interactions. In this example, responsive to the user's selection of "Bouncing," the application running on the monitoring device 104 presents GUI 900. Bouncing corresponds to a user-POD interaction that develops skills to push-off onto the toes and improves user's reliance on the POD by improving the user's balance and orientation. In response to the user's selection, the application presents a different GUI screen (for example, GUI 900) on the monitoring device. As described herein, the monitoring device 104 can communicate with the POD 102 to obtain gait parameter data. In this example, the gait parameter data can correspond to data from one or more force sensors 112, among other sensors.

In the illustrated embodiment of FIGS. 9A-9B, the GUI 900 includes various display objects such as a graphical indication 920 representing an amount of load placed on the POD 102, a repetition counter 944, a stick figure representation 932 of the selected user-POD interaction (in this case, Bouncing), a weight/load threshold marker 928, and a repetition threshold 926. The various indicators, or display objects, can be used to aid the user in improving the user-POD interaction. In some cases, the GUI 900 can include fewer, more, or different display objects, as desired. For example, the GUI 900 can include a success indicator or a timing indicator, as described herein.

The graphical indication 920 can be indicative of an amount of load placed on the POD 102 or the sound limb. For example, the graphical indication 920 can include a shaded region 940 which can represent a load on the POD 102. A relative size of the shaded region 940 can indicate an amount of load placed on the POD 102. That is, a larger shaded region can indicate that the user is loading the POD more heavily, while a smaller shaded region can indicate that the user is not loading the POD as heavily.

In the illustrated embodiments, the graphical indication 920 includes a bar display including a vertical bar that corresponds to an amount of load placed on the POD (such as load placed the toe of the POD). However, it will be understood that the loading and/or weight distribution of the POD can be presented by the graphical indication 920 in various ways.

The repetition counter 944 can provide a representation of a number of successful repetitions that the user is to compete for the user-POD interaction. In the illustrated embodiment, the repetition counter 944 is shown as a countdown timer that starts out with the total number of suggested repetitions and decrements as a successful repetition is completed. In some cases, after a successful repetition is completed, the monitoring device can decrement the repetition counter 944 when the user satisfies the weight/load threshold (for example, as described herein with respect to FIGS. 7A-7D).

In some cases, the GUI 900 will provide a success indicator (not shown) that is indicative a successful repetition. In some cases, to proceed to the next repetition, the monitoring device 104 can determine that the user transfers sufficient weight off the POD 102 such that the load or weight distribution does not satisfy the repetition threshold 926. It will be understood that the repetition counter 944 can be implemented in a variety of ways. For example, the repetition counter 944 can count up to an amount of suggested repetitions (for example, 10 repetitions).

In response to the user increasing or decreasing the load on the POD 102, the POD 102 or monitoring device 104 can detect the shift or change in load. The monitoring device 104, in turn, can update the display in real-time with the weight distribution of the user on the GUI 900. As illustrated in image 902, the user can lean his weight forward onto his toes and raise his heels off the ground so as to move load to a toe area of the POD 102. When the user shifts his weight onto his toes, the shaded region of the vertical bar 922 of the GUI 900 stays below weight/load threshold marker 928, representing low load on the POD 102.

As illustrated in FIG. 9B, in response to the user lowering his heels (for example, as illustrated in image 904), the POD 102 or monitoring device 104 can detect an increased load and the monitoring device 104 can update the GUI 900 in real-time. The increased load may be a result of increased weight on the POD 102 and/or the force at which the user lowers his heels to the ground. In response to the increased load on the POD 102, the shaded region of the vertical bar 922 of the GUI 900 increases in size to represent increased load on the POD 102.

Based on the gait parameter data received from the POD 102, the monitoring device 104 can determine that the load on the POD 102 satisfies a weight/load threshold. Once the threshold load is satisfied, the monitoring device 104 can adjust (for example, increment or decrement) the repetition counter 944 to track a number of successful repetitions.

In some cases, based on a determination that the load on the POD 102 satisfies the weight/load threshold, the monitoring device 104 can cause on the GUI 900 of a success indicator, indicating that the weight/load threshold on the POD 102 was satisfied. In some cases, to proceed to the next repetition, the monitoring device 104 must subsequently determine that the load on the POD 102 does not satisfy repetition threshold 926. The user can repeat the user-POD interaction until a desired number of repetitions have been completed. Although each of states 902 and 904 illustrate a user holding on to a handrail, it will be understood that in some cases the handrail is unnecessary, or may be used for balancing purposes.

By interacting with the POD 102 in real-time and displaying the status or parameters of the POD 102 in real time to the user, the monitoring device 104 can improve the user-POD interaction. By improving the user-POD interaction, the system can prevent injuries and pain caused by user's incorrect use of the POD.

Sitting Down

FIGS. 10A-10D are diagrams illustrating embodiments of various states of a user-POD interaction for improving the user's symmetry while sitting down, and further illustrate a GUI 1000 of a monitoring device (such as monitoring device 104 of FIG. 1) in communication with the POD. The GUI 1000 includes various display objects that can be used to aid the user-POD interaction. In each of FIGS. 10A-10D, the display objects of the GUI 1000 can be updated in real time and can reflect a corresponding state (for example, state 1002, 1004, 1006, or 1008) of the user-POD interaction.

As described herein, a software application on the monitoring device 104 can present a GUI (for example, GUI 600 of FIG. 6) that permits the user to select from various unique user-POD interactions. In this example, responsive to the user's selection of "Sitting down," the application running on the monitoring device 104 presents GUI 1000. Sitting down corresponds to a user-POD interaction improves user's reliance on the POD by improving the user's symmetry and balance when transitioning to sit down. As described herein, the monitoring device 104 can communicate with various sensors of the POD 102 to obtain sensor information. As described herein, the monitoring device 104 can communicate with the POD 102 to obtain gait parameter data. In this example, the gait parameter data can correspond to data from a force sensor 112 and an angle sensor 116, among other sensors.

In the illustrated embodiment of 10A-10D, the GUI 1000 includes various display objects such as a graphical indication 1020. The graphical indication 1020 can include display objects such as a load indicator 1024 representing an amount of load placed on the POD 102 or sound limb, a braking indicator 1050, a stick figure representation 1032 of the selected user-POD interaction (in this case, Sitting down), a braking threshold marker 1048, a success indicator 1036, and a past results indicator 1046. The various indicators, or display objects, can be used to aid the user in improving the user-POD interaction. In some cases, the GUI 1000 can include fewer or more display objects as desired.

The load indicator 1024 can be indicative of an amount of load placed on the POD 102 or an amount of load placed on a sound limb of a user fitted with the POD 102. The load indicator 1024 can be shaded, colored, or otherwise configured to represent a load of the POD 102. That is, a first color (for example, red or yellow) can indicate that the load or weight distribution does not satisfy a weight/load threshold (for example, as described herein with respect to FIG. 7A-7D), while a second color (for example, green) can indicate that the load or weight distribution satisfies the weight/load threshold.

In the illustrated embodiments, the load indicator 1024 includes a plurality of regions, each corresponding to an amount of load placed on the POD. For example, a first region (for example, the top circle) can correspond to a determination that no or little load is being placed on the POD 102, the second region (for example, the middle circle) can correspond to a determination that load is being placed on the POD 102 but the load does not satisfy the weight/load threshold, and the third region (for example, the bottom circle) can correspond to a determination that load distribution satisfies the weight/load threshold. However, it will be understood that the loading and/or weight distribution of the POD 102, the sound limb, or both can be presented by the load indicator 1024 in various ways.

The braking indicator 1050 can be indicative of a parameter corresponding to the resistive braking effect of the POD 102. For example, as described herein, the braking parameter can include, but is not limited to, a current flowing through the POD 102 (for example, flowing through a coil of the POD 102), a magnetic field, a fluid viscosity, a magnitude of the shearing force/stress, a torque or torsional resistance generated, or a level of damping. In the illustrated embodiments, the braking indicator 1050 can be represented as a bar display that includes a vertical bar 1050 corresponding to the braking indicator of the POD. Shaded region 1040 of the vertical bar 1050 can represent a real time amount of the braking indicator. For example, a vertical bar with a larger shaded region can indicate that the POD is applying more braking power (for example, larger braking indicator), while a vertical bar with a smaller shaded region can indicate that the user applying less braking power (for example, smaller braking indicator). In some cases, the braking threshold marker 1048 can indicate an amount required by the shaded region 1040 to complete a successful repetition.

As described herein, the POD 102 can include one or more angle sensors configured to monitor a knee joint angle, which can be described as an angle between the shank of the POD and the user's thigh. In some cases, the knee joint angle is linked to the braking indicator 1050 such that the GUI 1000 may display the braking indicator 1050 (or the shaded region 1040 of the braking indicator 1050) only when the knee joint angle falls within a range of angles. In other words, based on a determination that the knee joint angle satisfies a first threshold knee joint angle (for example, 15, 20, 25, 30, 35, 40, or 45 degrees (+/−a few degrees)) and does not satisfy a second threshold knee joint angle (for example, 25, 30, 35, 40, 45, 50, or 55 degrees (+/−a few degrees)), the GUI 1000 can display the shaded region 1040 of the braking indicator 1050. Similarly, based on a determination that the knee joint angle does not satisfy the first threshold knee joint angle or satisfies the second threshold knee joint angle, the GUI 1000 might not display the shaded region 1040 of the braking indicator 1050. However, in some cases, the GUI 1000 can display the shaded region 1040 of the braking indicator 1050 without regard to the knee joint angle. In some cases, the GUI 1000 will provide a success indicator 1036 that is indicative a successful repetition.

In some cases, the GUI 1000 can also include a past results indicator 1046 that displays the maximum shaded region 1040 of the braking indicator 1050 that the user has achieved during the user-POD interaction. In the illustrated embodiments, the past results indicator 1046 can include a shadow-like shading that is different from the shading of shaded region 1040.

In response to the user increasing or decreasing the load on the POD 102, the POD 102 or the monitoring device 104 can detect the shift or change in load and the monitoring device 104, in turn, can update the load indicator 1024 in real-time with the weight distribution of the user on the GUI 1000. As illustrated in image 1002, in response to the user holding his weight unevenly, the POD 102 can determine that the weight/load threshold is not satisfied and can update the GUI 1000 in real-time to reflect this.

As illustrated in FIG. 10B, in response to the symmetrically or substantially symmetrically loading his weight across the POD 102 and sound limb (for example, as illustrated in image 1004), the monitoring device 104 can update the load indicator 1024 in real-time. Furthermore, in response to a determination that the weight/load threshold is satisfied, the monitoring device 104 can monitor the knee joint angle. In response to a determination that the knee joint angle does not satisfy the first threshold (for example, 20 degrees), the monitoring device 104 either does not monitor the parameter corresponding to the resistive braking effect of the POD 102 or does not display the shaded region 1046 of the braking parameter 1050.

Figures 10C, 10D:
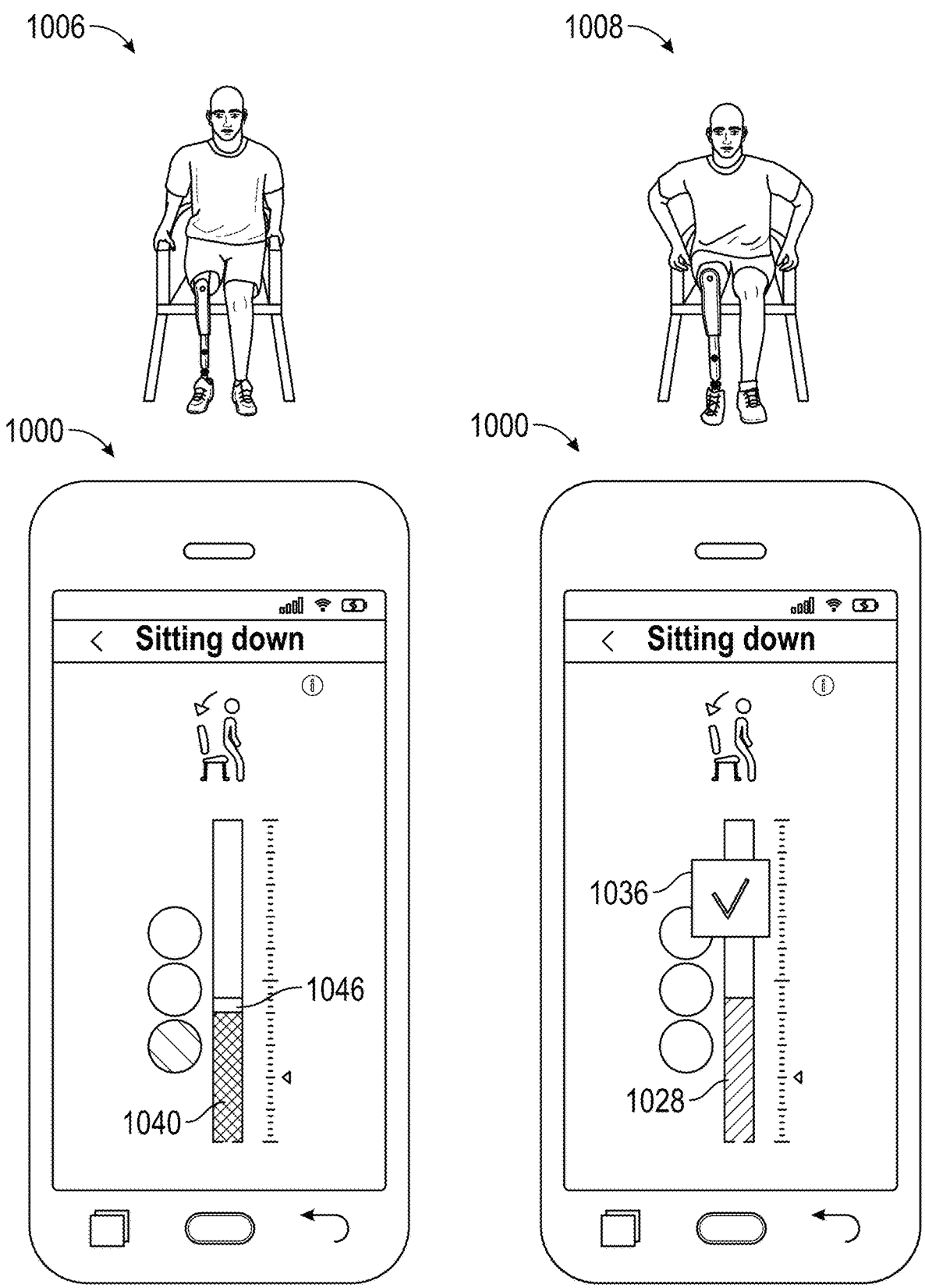

As illustrated in FIG. 10C, based on the gait parameter data received from the POD 102, the monitoring device 104 can determine that the weight distribution of the user satisfies the weight/load threshold. In addition, based on the gait parameter data, the monitoring device 104 can determine that the knee joint angle satisfies the first angle threshold. In response to these determinations, the monitoring device 104 can update the braking indicator 1050 in real-time. In the illustrated embodiment, the GUI 1000 illustrates both the shaded region 1040 and the past results indicator 1046 in the braking indicator 1050.

As illustrated in FIG. 10D, based on the gait parameter data received from the POD 102, the monitoring device 104 can determine that the user has maintained the weight distribution, and that the knee joint angle continues to satisfy the first angle threshold, but does not satisfy the second angle threshold (for example, 40 degrees). Based on these determinations, and further based on a determination that the braking threshold is satisfied, the monitoring device 104 can cause on the GUI 1000 of a success indicator 1036, indicating that the user completed a successful repetition of the user-POD interaction. The user can repeat the user-POD interaction until a desired number of repetitions have been completed.

By interacting with the POD 102 in real-time and displaying the status or parameters of the POD 102 in real time to the user, the system can improve the user-POD interaction. By improving the user-POD interaction, the system can prevent injuries and pain caused by user's incorrect use of the POD.

Stair Descent

Figures 11A, 11B:
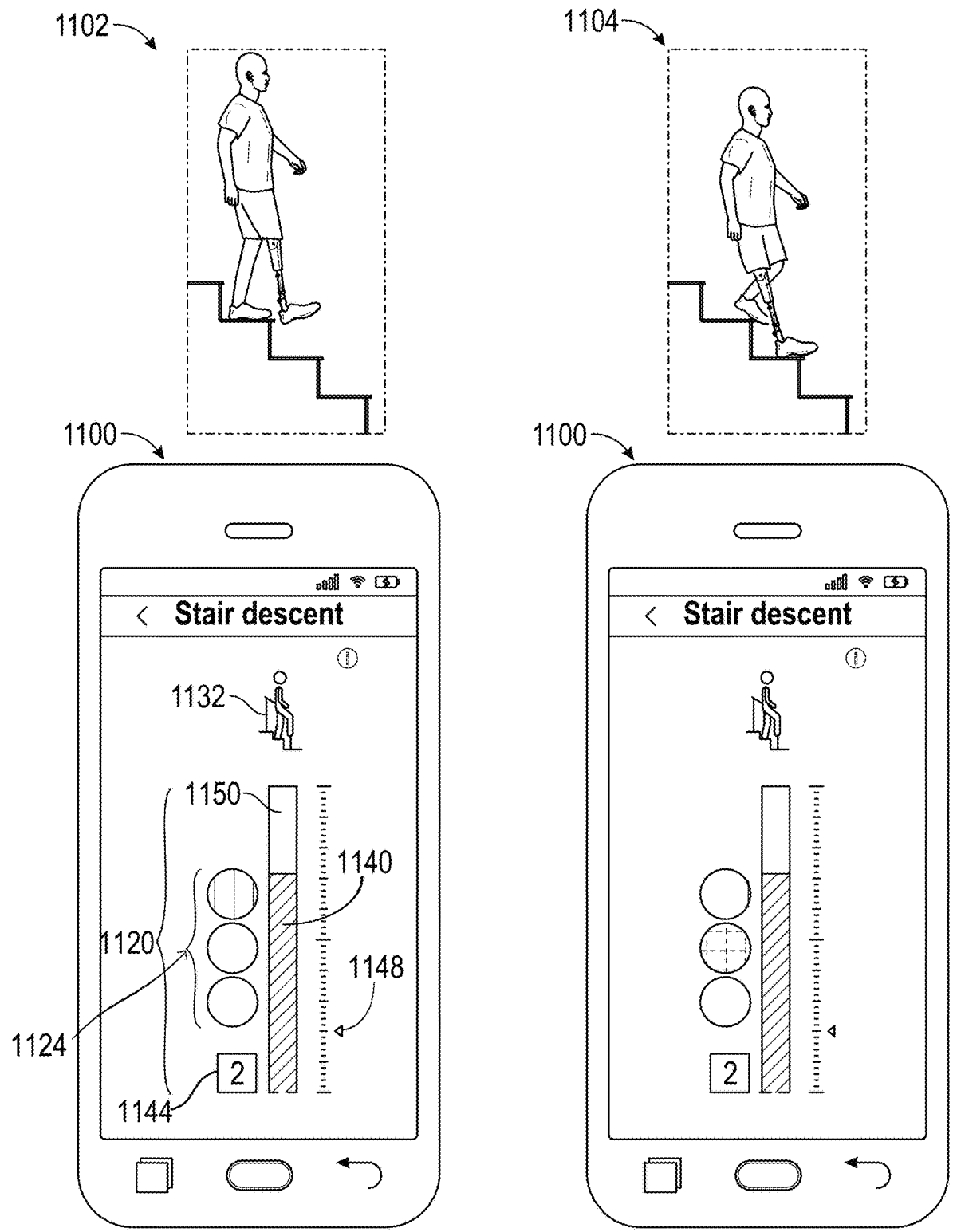
FIGS. 11A-11C are diagrams illustrating embodiments of various states of a user-POD interaction for improving the user's symmetry while descending stairs, and further illustrate a GUI of a monitoring device in communication with the POD.
Figure 11C:
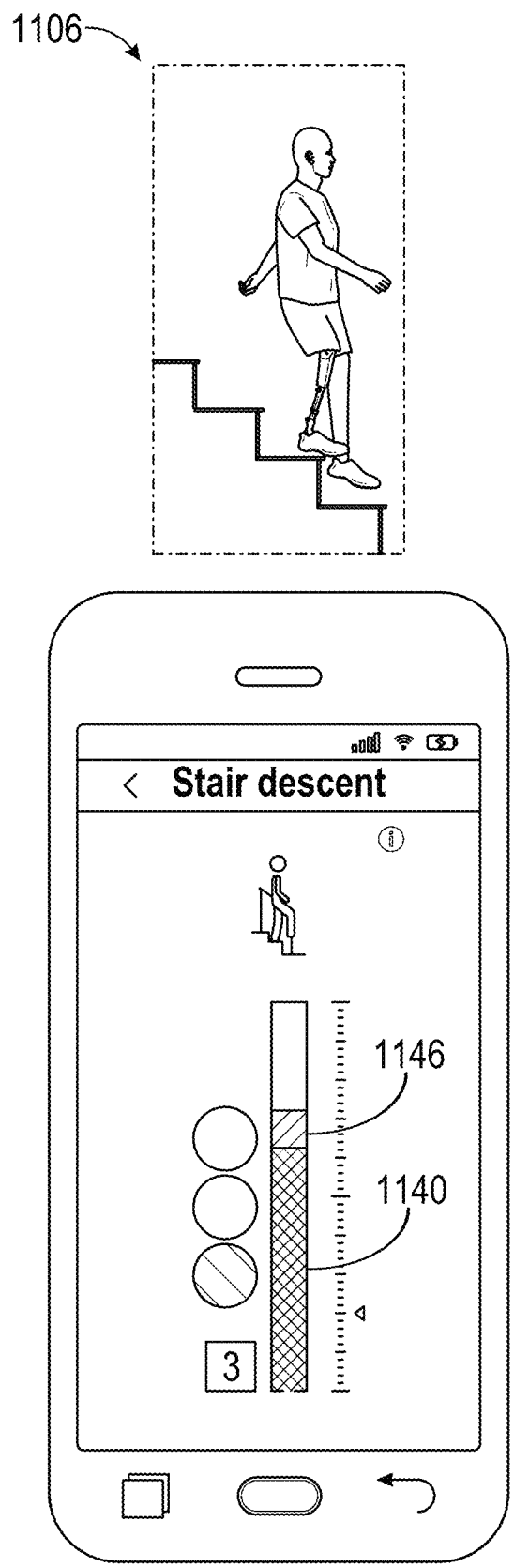

FIGS. 11A-11C are diagrams illustrating embodiments of various states of a user-POD interaction for improving load of the POD while descending stairs, and further illustrate a GUI 1100 of a monitoring device (such as monitoring device 104 of FIG. 1) in communication with the POD. The GUI 1100 includes various display objects that can be used to aid the user-POD interaction. In each of FIGS. 11A-11C, the display objects of the GUI 1100 can be updated in real time and can reflect a corresponding state (for example, state 1102, 1104, or 1106) of the user-POD interaction.

As described herein, a software application on the monitoring device 104 can present a GUI (for example, GUI 600 of FIG. 6) that permits the user to select from various unique user-POD interactions. In this example, responsive to the user's selection of "Stair Descent," the application running on the monitoring device 104 presents GUI 1100. Stair Descent corresponds to a user-POD interaction improves user's reliance on the POD by improving the user's symmetry and balance when descending stairs. As described herein, the monitoring device 104 can communicate with the POD 102 to obtain gait parameter data. In this example, the gait parameter data can correspond to data from a force sensor 112 and an angle sensor 116, among other sensors.

In the illustrated embodiment of 11A-11C, the GUI 1100 includes various display objects such as a graphical indication 1120. The graphical indication 1120 can include display objects such as a load indicator 1124 representing an amount of load placed on the POD 102, a braking indicator 1150, a stick figure representation 1132 of the selected user-POD interaction (in this case, Stair Descent), a braking threshold marker 1148, a repetition counter 1144, and a past results indicator 1146. The various indicators, or display objects, can be used to aid the user in improving the user-POD interaction. In some cases, the GUI 1100 can include fewer or more display objects as desired.

The load indicator 1124 can be indicative of an amount of load placed on the POD 102 or an amount of load placed on a sound limb of a user fitted with the POD 102. The load indicator 1124 can be shaded, colored, or otherwise configured to represent a load of the POD 102. That is, a first color (for example, red or yellow) can indicate that the load or weight distribution does not satisfy a weight/load threshold (for example, as described herein with respect to FIG. 7A-7D), while a second color (for example, green) can indicate that the load or weight distribution satisfies the weight/load threshold.

In the illustrated embodiments, the load indicator 1124 includes a plurality of regions, each corresponding to an amount of load placed on the POD. For example, a first region (for example, the top circle) can correspond to a determination that no load is being placed on the POD, the second region (for example, the middle circle) can correspond to a determination that load is being placed on the POD but the load does not satisfy the weight/load threshold, and the third region (for example, the bottom circle) can correspond to a determination that load distribution satisfies the weight/load threshold. However, it will be understood that the loading and/or weight distribution of the POD, the sound limb, or both can be presented by the load indicator 1124 in various ways.

The braking indicator 1150 can be indicative of a parameter corresponding to the resistive braking effect of the POD 102. For example, as described herein, the braking parameter 1150 can include, but is not limited to, a current flowing through the POD, the magnetic field, a fluid viscosity, a magnitude of the shearing force/stress, a torque or torsional resistance generated, or a level of damping. In the illustrated embodiments, the braking indicator 1150 can be represented as a bar display that includes a vertical bar 1150 corresponding to the braking indicator 1150 of the POD 102. Shaded region 1140 of the vertical bar 1150 can represent a real time amount of the braking. For example, a vertical bar with a larger shaded region can indicate that the POD 102 is applying more braking power (for example, larger braking indicator), while a vertical bar with a smaller shaded region can indicate that the user applying less braking power (for example, smaller braking indicator). In some cases, the braking threshold marker 1148 can indicate an amount required by the shaded region 1140 to complete a successful repetition.

As described herein, the POD includes one or more angle sensors configured to monitor a knee joint angle. In some cases, the knee joint angle is linked to the braking indicator 1150 such that the GUI 1100 may display the braking indicator 1150 (or the shaded region 1140 of the braking indicator 1150) only when the knee joint angle falls within a range of angles. In other words, based on a determination that the knee joint angle satisfies a first threshold knee joint angle (for example, 20, 25, 30, 35, 40, 45, or 50 degrees (+/−a few degrees)) and does not satisfy a second threshold knee joint angle (for example, 30, 35, 40, 45, 50, 55 or 60 degrees (+/−a few degrees)), the GUI 1100 can display the shaded region 1140 of the braking indicator 1150. Similarly, based on a determination that the knee joint angle does not satisfy the first threshold knee joint angle or satisfies the second threshold knee joint angle, the GUI 1100 might not display the shaded region 1140 of the braking indicator 1150. However, in some cases, the GUI 1100 can display the shaded region 1140 of the braking indicator 1150 without regard to the knee joint angle. In some cases, the GUI 1100 will provide a success indicator that is indicative a successful repetition.

In some cases, the GUI 1100 can also include a past results indicator 1146 that displays the maximum shaded region 1140 of the braking indicator 1150 that the user has achieved during the user-POD interaction. In the illustrated embodiments, the past results indicator 1146 can include a shadow-like shading that is different from the shading of shaded region 1140.

The repetition counter 1144 can provide a representation of a number of successful repetitions that the user competed for the user-POD interaction. In the illustrated embodiment, the repetition counter 1144 is shown as a count up timer that starts out with zero repetitions and increment as a successful repetition is completed. In some cases, the GUI 1100 will provide a success indicator (not shown) that is indicative a successful repetition.

In response to the user increasing or decreasing the load on the POD 102, the POD 102 or the monitoring device 104 can detect the shift or change in load and the monitoring device 104, in turn, can update the load indicator 1124 in real-time with the weight distribution of the user on the GUI 1100. As illustrated in image 1102, in response to the POD 102 being unloaded, the POD 102 or the monitoring device 104 can determine that the weight/load threshold is not satisfied and the GUI 1100 can be updated in real-time to reflect this. Further, because the weight/load threshold is not satisfied, the monitoring device 104 may not monitor the knee angle parameter or simply may not display the shaded region 1140 of the braking parameter 1150. However, as described above, the GUI 1100 can display the past results indicator 1146.

As illustrated in FIG. 11B, in response to the loading the POD 102 (for example, as illustrated in image 1106), the monitoring device 104 can update the load indicator 1124 in real-time. However, in this example, the POD remains insufficiently loaded. Thus, because the weight/load threshold is not satisfied, the monitoring device 104 either does not monitor the knee angle parameter or simply does not display the shaded region 1140 of the braking indicator 1050. However, in this example, the display on the GUI 1100 continues to show the past results indicator 1146.

As illustrated in FIG. 11C, based on the gait parameter data received from the POD 102, the monitoring device 104 can determine that the load on the POD satisfies the load threshold. In addition, based on the gait parameter data, the monitoring device 104 can determine that the knee joint angle satisfies the first angle threshold (for example, 30 degrees) and does not satisfy a second angle threshold (for example, 50 degrees). In response to these determinations, the monitoring device receives in real time gait parameter data corresponding to the resistive braking effect of the POD 102, and can update the braking indicator 1150 in real-time. In the illustrated embodiment, the GUI 1100 illustrates both the shaded region 1140 and the past results indicator 1146 in the braking indicator 1150. In addition, based on a determination that the shaded region 1140 satisfied the braking threshold, the monitoring device 104 causes the repetition counter 1144 to increment to indicate a successful repetition. In some cases, the monitoring device 104 can also cause on the GUI 1100 of a success indicator.

By interacting with the POD 102 in real-time and displaying the status or parameters of the POD 102 in real time to the user, the monitoring device 104 can improve the user-POD interaction. By improving the user-POD interaction, the monitoring device 104 can prevent injuries and pain caused by user's incorrect use of the POD.

Stair Ascent

Figure 12C:
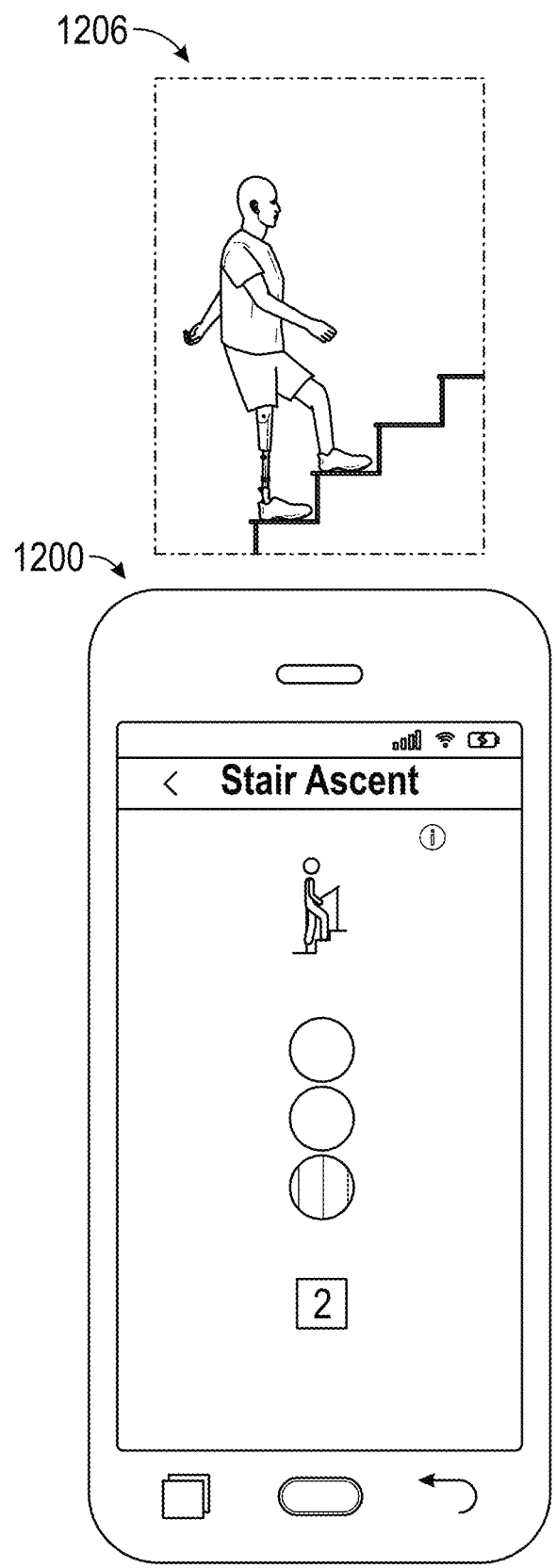

FIGS. 12A-12C are diagrams illustrating embodiments of various states of a user-POD interaction for improving the user's symmetry while ascending stairs, and further illustrate a GUI of a monitoring device in communication with the POD. The GUI 1200 includes various display objects that can be used to aid the user-POD interaction. In each of FIGS. 12A-12C, the display objects of the GUI 1200 can be updated in real time and can reflect a corresponding state (for example, state 1202, 1204, 1206, 1208) of the user-POD interaction.

As described herein, a software application on the monitoring device 104 can present a GUI (for example, GUI 600 of FIG. 6) that permits the user to select from various unique user-POD interactions. In this example, responsive to the user's selection of "Stair ascent," (not illustrated in FIG. 6) the application running on the monitoring device 104 presents GUI 1200. Stair Ascent corresponds to a user-POD interaction improves user's reliance on the POD by improving the user's symmetry and balance when ascending stairs. As described herein, the monitoring device 104 can communicate with the POD 102 to obtain gait parameter data. In this example, the gait parameter data can correspond to data from a force sensor 112, an accelerometer 114, and an angle sensor 116, among other sensors.

In the illustrated embodiment of 12A-12C, the GUI 1200 includes various display objects such as a graphical indication. The graphical indication 1220 can include display objects such as a load/angle indicator 1224 representing at least one of a ground contact threshold, a knee angle threshold or an acceleration of the POD, a stick figure representation 1232 of the selected user-POD interaction (in this case, Stair Ascent), and a repetition counter 1244. The various indicators, or display objects, can be used to aid the user in improving the user-POD interaction. In some cases, the GUI 1200 can include fewer, additional, or different display objects, as desired.

As described herein, the POD includes one or more force sensors configured to sense load on the POD 102 and one or more angle sensors configured to measure a knee joint angle. The load/angle indicator 1224 can be indicative of data from a combination of one or more of the force sensors or the angle sensors. For example, the load/angle indicator 1224 can provide an indication of ground contact and/or a knee rotation angle. The load/angle indicator 1224 can be shaded, colored, or otherwise configured to provide a positive or negative indication regarding the user's performance of the user-POD interaction.

For example, based on a determination that the POD is on a step (for example, the force sensor indicates ground contract), the shading or color of the load/angle indicator 1224 can be based on the knee rotation angle. For example, if the knee rotation satisfies a first threshold knee joint angle (for example, 20, 25, 30, 35, 40, 45, or 50 degrees (+/−a few degrees)) and does not satisfy a second threshold knee joint angle (for example, 30, 35, 40, 45, 50, 55 or 60 degrees (+/−a few degrees)), the load/angle indicator 1224 can provide a positive indication (for example, a green light) that the user can continue with the user-POD interaction. If the knee rotation does not satisfy the first threshold knee joint angle and/or satisfies a second threshold knee joint angle, the load/angle indicator 1224 can provide a negative indication (for example, a red or yellow light), indicating that the user should adjust the knee joint angle. In some cases, in addition or alternatively to a positive or negative indication, the GUI can include one or more indicators that identify or indicate how far (for example, in degrees) a user is from satisfying or not satisfying a threshold. For example, the indicator can include a color, a sliding scale (for example, a moving bar that can pass a threshold market), a number (for example, corresponding to the knee rotation angle), or instructions (for example, "bend knee", "straighten knee"). However, it will be noted that any of various indicators can be used.

As another example, based on a determination that the POD is not on a step (for example, the force sensor indicates no or little ground contract), the shading or color of the load/angle indicator 1224 can be based on the knee rotation angle. For example, if the knee rotation satisfies a third threshold knee joint angle (for example, 20, 25, 30, 35, 40, 45, or 50 degrees (+/−a few degrees)) and does not satisfy a fourth threshold knee joint angle (for example, 30, 35, 40, 45, 50, 55 or 60 degrees (+/−a few degrees)), the load/angle indicator 1224 can provide a positive indication (for example, a green light) that the user can continue with the user-POD interaction. If the knee rotation does not satisfy the third threshold knee joint angle and/or satisfies a fourth threshold knee joint angle, the load/angle indicator 1224 can provide a negative indication (for example, a red or yellow light), indicating that the user should adjust the knee joint angle.

In addition or alternatively, the POD can include one or more accelerometers configured to measure an acceleration of the POD. In some cases, if the POD is not on a step, the load/angle indicator 1224 will provide a positive or negative indication based on the speed or acceleration of the POD. For example, if the speed or acceleration satisfies an acceleration threshold, a positive indication can be presented. In contrast, if the speed or acceleration does not satisfy the acceleration threshold, a negative indication can be presented.

In some cases, the shading or color of the load/angle indicator 1224 can be based the acceleration of the POD. For example, if acceleration satisfies an acceleration threshold, the load/angle indicator 1224 can provide a positive indication (for example, a green light) that the user can continue with the user-POD interaction. If the acceleration does not satisfy the acceleration threshold, the load/angle indicator 1224 can provide a negative indication (for example, a red or yellow light), indicating that the user should adjust the acceleration. In some cases, the GUI can indicate whether the user should increase or decrease the acceleration of the POD to satisfy the acceleration threshold.

The repetition counter 1244 can provide a representation of a number of successful repetitions that the user competed for the user-POD interaction. In the illustrated embodiment, the repetition counter 1244 is shown as a count up timer that starts out with zero repetitions and increment as a successful repetition is completed. In some cases, the GUI 1200 will provide a success indicator (not shown) that is indicative a successful repetition.

The monitoring device 104 can update the load/angle indicator 1224 in real-time to indicate whether user to correctly performing the user-POD interaction. This may be based, for example, one whether the POD is contacting the ground, whether the knee joint angle is suitable, and/or whether the acceleration of the POD is suitable.

As illustrated in image 1202, based on a determination that the POD is not contacting the ground, the monitoring device can look to the knee rotation angle and/or the acceleration of the POD to determine whether the user is correctly performing the Stair Ascent. In this example, the knee joint angle does not satisfy the first threshold knee joint angle. In addition, the acceleration of the POD does not satisfy the acceleration threshold. Accordingly, the load/angle indicator 1224 will provides a negative indication, which in this case corresponds to a shaded middle circle of the load/angle indicator 1224. However, as described herein, the negative indication can include any of various indications. For example, the GUI 1200 can display instructions or guidance to the user.

As illustrated in image 1204, based on a determination that the POD is contacting the ground, the monitoring device can look to the knee rotation angle to determine whether the user is correctly performing the Stair Ascent. In this example, based on the angle sensor data, the monitoring device 104 can determine that the knee joint angle satisfies a third threshold knee joint angle and does not satisfy a fourth threshold knee joint angle. In response to these determinations, the monitoring device 104 can cause the load/angle indicator 1224 to provide a positive indication, which in this case corresponds to a shaded bottom circle of the load/angle indicator 1224. However, as described herein, the negative indication can include any of various indications.

As illustrated in image 1206, based on a determination that the user successfully completed a repetition (for example, successfully traversed a stair), monitoring device 104 can adjust (for example, increment or decrement) the repetition counter 1244 to track a number of successful repetitions. In some cases, the monitoring device 104 can also cause on the GUI 1200 of a success indicator.

By interacting with the POD 102 in real-time and displaying the status or parameters of the POD 102 in real time to the user, the system can improve the user-POD interaction. By improving the user-POD interaction, the system can prevent injuries and pain caused by user's incorrect use of the POD.

Flow Diagrams

Figure 13:
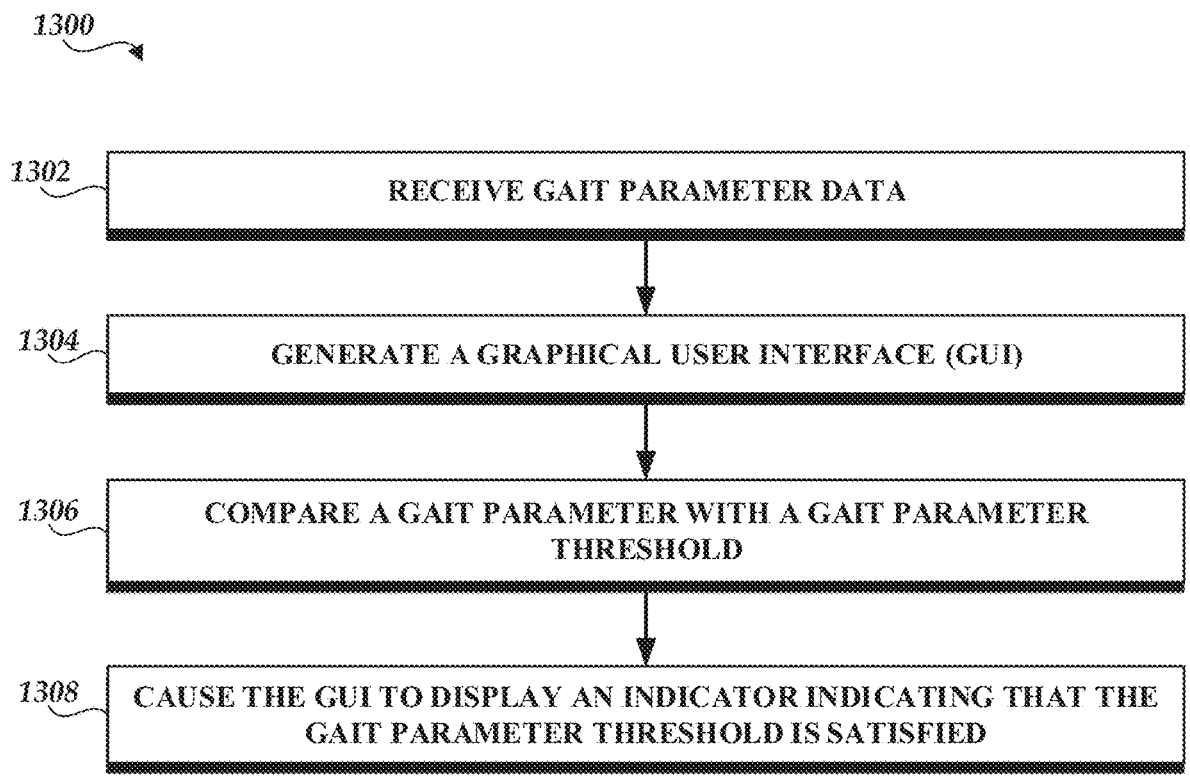
FIG. 13 is a flow diagram illustrative of an embodiment of a routine implemented by a system for improving interactions with a prosthetic or orthotic device.

FIG. 13 is a flow diagram illustrative of an embodiment of a routine 1300 implemented by a system for improving interactions with a prosthetic or orthotic device. One skilled in the relevant art will appreciate that the elements outlined for routine 1300 can be implemented by one or more computing devices that are associated with the system 100, such as the monitoring device 104 and/or the POD 102. Accordingly, routine 1300 has been logically associated as being generally performed by the monitoring device 104 of FIG. 1. However, the following illustrative embodiment should not be construed as limiting. Furthermore, it will be understood that the various blocks described herein with reference to FIG. 13 can be implemented in a variety of orders. For example, the monitoring device 104 can implement some blocks concurrently or change the order, as desired. Furthermore, it will be understood that fewer, more, or different blocks can be used as part of the routine 1300.

At block 1302, a monitoring device 104 communicates with POD 102. As described herein, the POD can include a sensor module comprising one or more various sensors. The one or more various sensors can be configured to measure one or more parameters during locomotion of a user fitted with the POD. In some cases, the locomotion can correspond to at least one of: the user shifting weight from the POD to a sound limb (for example, as illustrated in FIGS. 7A-7D), the user shifting weight from the sound limb to the POD (for example, as illustrated in FIGS. 7A-7D), a user shifting body weight forward (for example, as illustrated in FIGS. 8A-8D), or a user shifting body weight backward (for example, as illustrated in FIGS. 8A-8D), the user shifting weight from a toe of the POD to a heel of the POD (for example, as illustrated in FIGS. 9A-9B), the user shifting weight from the heel of the POD to the toe of the POD (for example, as illustrated in FIGS. 9A-9B), the user sitting down (for example, as illustrated in FIGS. 10A-10D), the user descending stairs (for example, as illustrated in FIGS. 11A-11C), or the user ascending stairs (for example, as illustrated in FIGS. 12A-12C). However, it will be understood that the locomotion can correspond to various other movements by the user, such as rising from a seated position, walking laterally, braiding (for example, crossing one foot over the other), leg kicks, agility drills, or the like.

During the communication between the monitoring device 104 and the POD 102, the monitoring device 102 can receive gait parameter data from the POD over time. In some cases, the gait parameter data can include sensor data measured by the one or more sensors of the sensor module. For example, the monitoring device can receive the gait parameter data (for example, sensor data) and based on the gait parameter data, the monitoring device 104 can determine one or more gait parameters. As described herein, a gait parameter can include, but is not limited to, a ground interaction, a user weight, an amount of load placed on the POD, an amount of load placed on the sound limb, a weight distribution between the POD and sound limb, a shank angle, a joint angle, or a braking power of the POD.

In addition or alternatively, in some cases, the gait parameter data can include information indicative of one or more gait parameters. For example, the POD 102 (for example, the controller 126) can use sensor data from the sensor module to determine one or more gait parameters. Accordingly, the gait parameter data received by the monitoring device 104 can include sensor data (for example, raw sensor data) and/or data indicative of one or more gait parameters (for example, data processed by the POD).

At block 1304, the monitoring device can generate in real time a graphical user interface that displays a graphical indication of one or more of the gait parameters over the time. For example, the monitoring device 104 can be implemented as any of various computing devices including, but not limited to, a processor, a cell phone, smart phone, a tablet, a computer, a laptop, or the like. A software application residing on the monitoring device 104 can generate a GUI that displays a visual indication of at least one determined gait parameter. As described above, the at least one gait parameter can be determined by the POD 102 and/or the monitoring device 104.

At block 1306, the monitoring device can compare the gait parameter with a gait parameter threshold. In some cases, the gait parameter threshold can correspond to objective thresholds for improving a user-POD interaction (for example, L-R shift, F-B shift, Bouncing, Sitting Down, Stair Descent, Stair Ascent or the like). For example, the gait parameter threshold can correspond to good or correct gait movements by the user. Accordingly, by requiring the user to satisfy or pass a gait parameter threshold, the monitoring device 104 can improve the user's reliance on the POD.

At block 1308, the monitoring device can cause display on the GUI of an indicator indicative that the gait parameter threshold is satisfied. For example, the GUI can include a success indicator indicating a successful repetition of the user-POD interaction. By completing a successful repetition, the user can be appropriately trained increasing or decreasing the amount of weight the user places on the POD 102, thereby improving the user's gait. Accordingly, by presenting an indicator that the gait parameter threshold is satisfied, the monitoring device is advantageously providing a visual quantification of good gait, thereby providing objective information to improve user-POD interaction. By improving the user-POD interactions, the GUI can prevent injuries and pain caused by user's incorrect use of the POD.

It will be understood that the various blocks described herein can be implemented in a variety of orders, and that the monitoring device 104 can implement one or more of the blocks concurrently and/or change the order, as desired. For example, the monitoring device 104 can concurrently receive the gait parameter data and generate a GUI. Similarly, the monitoring device 104 can concurrently receive gait parameter data, compare a gait parameter with a gait parameter threshold, and/or cause display on the GUI of an indicator indicating that the gait parameter threshold is satisfied.

Furthermore, it will be understood that fewer, more, or different blocks can be used as part of the routine 1300. For example, the routine 1300 can include blocks for determining a gait parameter corresponding to the gait parameter data. Similarly, the gait parameter can be a first gait parameter and the gait parameter threshold can be a gait parameter. Accordingly, additional blocks can be used for determining a second gait parameter, comparing a second gait parameter with a second gait parameter threshold, or displaying an indicator that the second gait parameter threshold is satisfied. Furthermore, the monitoring device 104 can cause display on the GUI of a variety of display objects, as described herein. In some cases, the routine 1300 can omit certain blocks, such as, but not limited to, blocks 1302, 1306, and/or 1308. For example, in some embodiments, the system may not receive gait parameter data, but instead can retrieve stored gait parameter data from memory.

Figure 14:
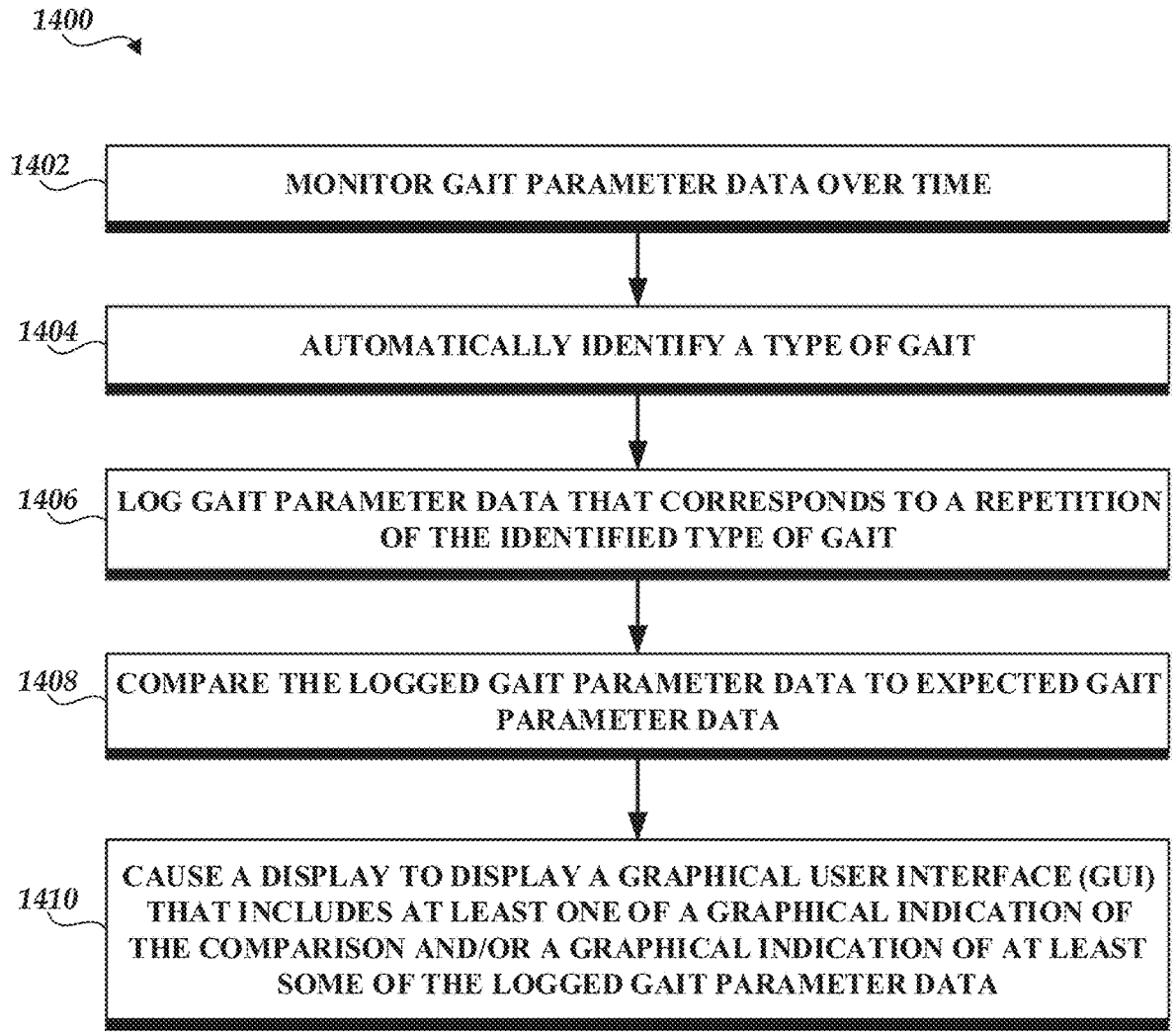
FIG. 14 is a flow diagram illustrative of an embodiment of a routine implemented by a system for improving interactions with a prosthetic or orthotic device.

FIG. 14 is a flow diagram illustrative of an embodiment of a routine 1400 implemented by a system for improving interactions with a POD. One skilled in the relevant art will appreciate that the elements outlined for routine 1400 can be implemented by one or more computing devices that are associated with the system 100, such as the monitoring device 104 and/or the POD 102. Accordingly, routine 1400 has been logically associated as being generally performed by the monitoring device 104 of FIG. 1. However, the following illustrative embodiment should not be construed as limiting. Furthermore, it will be understood that the various blocks described herein with reference to FIG. 14 can be implemented in a variety of orders. For example, the monitoring device 104 can implement some blocks concurrently or change the order, as desired. Furthermore, it will be understood that fewer, more, or different blocks can be used as part of the routine 1400.

At block 1402, monitoring device 104 can monitor gait parameter data over time. For example, as described herein, monitoring device 104 can communicate with POD 102. The POD can include a sensor module comprising one or more various sensors, and the sensors can be configured to measure one or more parameters during locomotion of a user fitted with the POD.

In some cases, the gait parameter data can correspond to daily life activities of the user. For example, in some cases, the user can use the GUI (for example, GUI 600 of FIG. 6) to initiate monitoring of a user-POD interaction (such as L-R shift, F-B shift, Bouncing, Sitting Down, Stair Descent, or Stair Ascent), and the monitoring device 102 can provide real time feedback of the user's movements and indicate successful repetitions of the selected user-POD interaction. However, in some cases, the monitoring device 104 can additionally or alternatively monitor gait parameter data during the user's daily life activities to determine how well the user initiated user-POD interactions are translating to the user's daily life.

At block 1404, the monitoring device 104 can automatically identify a type of gait based on the monitored gait parameter data. For example, although the user may not have initiated a user-POD interaction, throughout his day, he may perform movements which correspond to one or more of the identified user-POD interactions. The monitoring device 104 can monitor the gait parameter data over time to determine if or when the user's movement corresponds to an identified user-POD interaction. Based on a determination that the user's movement (or sensor data) corresponds to an identified user-POD interaction, the monitoring device 104 can automatically determine a type of gait (for example, L-R shift, F-B shift, Bouncing, Sitting Down, Stair Descent, or Stair Ascent).

For example, based on a determination that the user is shifting weight from the POD to a sound limb or the user is shifting weight from the sound limb to the POD, the monitoring device can identify the L-R type of gait. As another example, based on a determination that a user is shifting body weight forward or shifting body weight backward, the monitoring device 104 can identify the F—B type of gait. As another example, based on a determination a user is shifting weight from a toe of the POD to a heel of the POD or that the user is shifting weight from the heel of the POD to the toe of the POD, the monitoring device 104 can identify the Bouncing type of gait. As another example, based on force sensor and/or angle sensor data, the monitoring device 104 can identify the Sitting Down type of gait. As another example, based on force sensor and/or angle sensor data, the monitoring device 104 can identify the Stair Descent type of gait. As another example, based on force sensor, angle sensor, and/or accelerometer data, the monitoring device 104 can identify the Stair Ascent type of gait.

At block 1406, the monitoring device 104 can log gait parameter data that corresponds to a repetition of the identified type of gait. To get an accurate sense of how the user is performing in daily life, it can be advantageous to log gait associated with real life activities. However, a single movement (for example, a subtle shift of the body weight from one side to the other) may not be indicative of the user's daily life performance. Accordingly, in some cases, the monitoring device 104 will only log gait parameter data based on a determination that the user performed a successful repetition (as described herein) of the identified type of gait. However, in some cases, the monitoring device 104 can log all gait parameter data and/or log all gait parameter data corresponding to a specific type of gait.

At block 1408, the monitoring device 104 can compare the logged gait parameter data to expected gait parameter data. For example, the expected gait parameter gait can correspond to a good gait, as objectively determined based on loading, angles, etc. In addition or alternatively, the expected gait parameter gait can correspond to gait parameter data received when the user initiated a user-POD interaction, for example, using GUI 600. Thus, the monitoring device 104 can compare user initiated user-POD interaction data to user-POD interaction data received during the user's daily life.

At block 1410, the monitoring device 104 can cause a display to display a graphical user interface (GUI) that includes at least one of a graphical indication of the comparison and/or a graphical indication of at least some of the logged gait parameter data. For example, the graphical indication can include one or more graphs or charts which identify the logged gait parameter data and the expected gait parameter data. Accordingly, the graphical indication can provide a visual quantification of the user's gait during his daily life, thereby providing addition opportunities to improve user-POD interactions. This can advantageously provide the user with a tool to prevent injuries and pain caused by user's incorrect use of the POD.

It will be understood that the various blocks described herein can be implemented in a variety of orders, and that the monitoring device 104 can implement one or more of the blocks concurrently and/or change the order, as desired. For example, any of the monitoring, identifying, logging, comparing, or display can occur concurrently. Furthermore, it will be understood that fewer, more, or different blocks can be used as part of the routine 1400. For example, the routine 1400 can include blocks for determining a gait parameter corresponding to the gait parameter data. Furthermore, the monitoring device 104 can cause display on the GUI of a variety of display objects, as described herein. In some cases, the routine 1400 can omit certain blocks, such as, but not limited to, blocks 1402, 1406, and/or 1408. For example, in some embodiments, the system may not receive gait parameter data, but instead can retrieve stored gait parameter data from memory.

Example Embodiments

Various example embodiments of the disclosure can be described in view of the following Clauses:

Clause 1. A system for improving interactions with a prosthetic or orthotic device, the system comprising:
 a prosthetic or orthotic device (POD) comprising:
  a first limb member,
  a second limb member coupled to the first limb member via a joint, and
  a sensor module configured to measure one or more parameters relating to the POD; and
 a monitoring device configured to be in wireless communication with the POD and configured to:
 receive sensor data from the sensor module over time,
 determine a gait parameter associated with the POD over the time based at least in part on the received sensor data,
 generate in real time a graphical user interface (GUI) that includes a graphical indication of the gait parameter over the time,
 compare the determined gait parameter with one or more gait parameter thresholds, and
 based on a determination that the determined gait parameter satisfies the one or more gait parameter thresholds, cause display on the GUI of an indicator indicating the one or more gait parameter thresholds are satisfied.

Clause 2. The system of the previous Clause, wherein the sensor module is configured to measure the one or more parameters during locomotion of a user fitted with the POD.

Clause 3. The system of any of the previous Clauses, wherein the POD comprises a prosthetic knee.

Clause 4. The system of any of the previous Clauses, wherein the POD comprises a prosthetic foot.

Clause 5. The system of any of the previous Clauses, wherein the sensor module comprises a force sensor configured to measure an amount of load on the POD, wherein the sensor data comprises force sensor data.

Clause 6. The system of Clause 5, wherein the graphical indication is indicative of the amount of load placed on the POD or an amount of load placed on a sound limb of a user fitted with the POD.

Clause 7. The system of any of Clauses 5 or 6, wherein the gait parameter comprises the amount of load placed on the POD.

Clause 8. The system of any of Clauses 5 to 7, wherein the graphical indication comprises a first shaded region that represents the amount of load placed on the POD and a second shaded region that represents an amount of load placed on a sound limb of a user fitted with the POD.

Clause 9. The system of any of Clauses 5 to 8, wherein the one or more gait parameter thresholds comprises a load threshold corresponding to the amount of load placed on the POD, wherein the monitoring device is further configured to monitor the amount of load placed on the POD over the time, and wherein the displayed indicator indicates that the monitored amount of load satisfied the load threshold for a period of time.

Clause 10. The system of any of Clauses 5 to 9, wherein the sensor module is configured to measure the one or more parameters during locomotion of a user fitted with the POD.

Clause 11. The system of Clause 10, wherein the locomotion of the user corresponds to the user shifting weight from the POD to the sound limb.

Clause 12. The system of Clause 10, wherein the locomotion of the user corresponds to the user shifting weight from the sound limb to the POD.

Clause 13. The system of Clause 10, wherein the locomotion of the user corresponds to the user loading the user's toes.

Clause 14. The system of any of Clauses 5 to 13, wherein the graphical indication comprises a plurality of regions, wherein each of the plurality of regions corresponds to an amount of load placed on the POD.

Clause 15. The system of Clause 14, wherein the plurality of regions comprises a first region corresponding to a determination that gait parameter satisfies the one or more gait parameter thresholds, and a second region corresponding to a determination that gait parameter does not satisfy the one or more gait parameter thresholds.

Clause 16. The system of Clause 15, wherein the plurality of regions further comprises a third region corresponding to no load on the POD.

Clause 17. The system of Clause 16, wherein the monitoring device is further configured to determine that the determined gait parameter satisfies the one or more gait parameter thresholds based on a determination that the force sensor measures a threshold load.

Clause 18. The system of Clause 17, wherein the threshold load corresponds to a portion of the user's body weight.

Clause 19. The system of any Clauses 17 or 18, wherein the threshold load corresponds to half of the user's body weight.

Clause 20. The system of any of Clauses 5 to 19, wherein the sensor module further comprises a sensor configured to measure at least one of a braking torque applied by the POD, a braking power applied by the POD, a resistance provided by the POD, or a current flowing through the POD.

Clause 21. The system of Clause 20, wherein the gait parameter is a first gait parameter and the graphical indication is a first graphical indication, wherein the monitoring device is further configured to:
 determine a second gait parameter associated with the POD over the time based at least in part on the received sensor data, wherein the second gait parameter corresponds to the resistance provided by the POD,
 wherein the GUI further includes a graphical indication of the second gait parameter over the time, wherein the graphical indication of the second gait parameter is indicative of the resistance provided by the POD.

Clause 22. The system of Clause 21, wherein the second graphical indication comprises a shaded region that represents the amount of resistance provided by the POD.

Clause 23. The system of any of Clauses 21 or 22, wherein the second graphical indication comprises an indication of a maximum resistance provided by the POD over the time.

Clause 24. The system of any of Clauses 21 to 23, wherein the sensor module further comprises an angle sensor configured to measure a joint angle corresponding to an angle between the first limb member and the second limb member.

Clause 25. The system of any of Clauses 21 to 24, wherein the monitoring device is further configured to determine the joint angle based at least in part on data from the angle sensor.

Clause 26. The system of Clause 25, wherein the monitoring device is further configured to:
based at least in part on a determination that the joint angle satisfies a first angle threshold and does not satisfy a second angle threshold, cause the graphical indication of the second gait parameter to indicate the resistance provided by the POD.

Clause 27. The system of any of Clauses 25 to 26, wherein the monitoring device is further configured to:
based at least in part on a determination that the joint angle does not satisfy a first angle threshold or that the joint angle satisfies a second angle threshold, cause the graphical indication of the second gait parameter to indicate that zero resistance is provided by the POD.

Clause 28. The system of any of Clauses 25 to 27, wherein the first angle threshold corresponds to a joint angle within a first range of 15 to 25 degrees, wherein the second angle threshold corresponds to a joint angle within a second range of 35 to 45 degrees.

Clause 29. The system of any of Clauses 25 to 27, wherein the first angle threshold corresponds to a joint angle of 30 degrees, wherein the second angle threshold corresponds to a joint angle of 50 degrees.

Clause 30. The system of any of Clauses 10 to 29, wherein the locomotion of the user corresponds to the user sitting down.

Clause 31. The system of any of Clauses 10 to 29, wherein the locomotion of the user corresponds to the user descending stairs.

Clause 32. The system of any of Clauses 10 to 29, wherein the locomotion of the user corresponds to the user ascending stairs.

Clause 33. The system of any of Clauses 5 to 32, wherein the sensor module further comprises at least one of an acceleration sensor or an orientation sensor.

Clause 34. The system of Clause 33, wherein the at least one of the acceleration sensor or the orientation sensor comprises an accelerometer, gyroscope, orientation sensor, or gravity sensor.

Clause 35. The system of any of Clauses 33 or 34, wherein the monitoring device is further configured to determine a shank angle based at least in part on data from the at least one of the acceleration sensor or the orientation sensor.

Clause 36. The system of Clause 35, wherein the shank angle corresponds to an angle of a line of a shank of the POD relative to at least of a line of a foot of the POD or a walking surface.

Clause 37. The system of any of Clauses 35 or 36, wherein the gait parameter is a first gait parameter and the graphical indication is a first graphical indication, wherein the monitoring device is further configured to:
determine a second gait parameter associated with the shank angle, wherein the GUI further includes a graphical indication of the second gait parameter over the time, wherein the graphical indication of the second gait parameter is indicative of the shank angle or a distribution of load on the POD.

Clause 38. The system of Clause 37, wherein the display of the indicator indicating the one or more gait parameter thresholds are satisfied is further based on a determination that, over the time, a first shank angle threshold was satisfied and a second shank angle threshold was satisfied.

Clause 39. The system of any of Clauses 35-38, wherein the first shank angle threshold corresponds to load on a heel the POD and the second shank angle threshold corresponds to load on toes of the POD.

Clause 40. The system of any of Clauses 10 to 39, wherein the locomotion of the user corresponds to the user shifting body weight forward or shifting body weight backward.

Clause 41. A method for improving interactions with a prosthetic or orthotic device (POD), the method comprising:
monitoring over time one or more gait parameters of a POD during locomotion of a user;
automatically identifying a type of gait based on the one or more gait parameters;
logging the one or more gait parameters corresponding to repetitions of the identified type of gait;
comparing the logged gait parameters to expected gait parameters corresponding to the identified type of gait; and
causing a display to display a graphical user interface (GUI) that includes a graphical indication of the comparison.

Clause 42. The method of Clause 41, wherein the gait parameter comprises an amount of load placed on the POD.

Clause 43. The method of Clause 42, wherein the type of gait corresponds to the user shifting body weight from at least one of left to right or right to left.

Clause 44. The method of any of Clauses 42 to 43, wherein the type of gait corresponds to the user shifting weight on the toes of the user and bouncing.

Clause 45. The method of any of Clauses 42 to 44, wherein the gait parameter further comprises a resistance provided by the POD.

Clause 46. The method of Clause 45, wherein the gait parameter is a first gait parameter, wherein the method further comprises determining a second gait parameter corresponding to a joint angle, wherein the joint angle is an angle between a first limb member and a second limb member of the POD, wherein the second limb member is coupled to the first limb member via a joint.

Clause 47. The method of Clause 46, wherein the type of gait corresponds to the user sitting down.

Clause 48. The method of Clause 46, wherein the type of gait corresponds to the user descending stairs.

Clause 49. The method of Clause 46, wherein the type of gait corresponds to the user ascending stairs.

Clause 50. The method of any of Clauses 42 to 49, wherein the gait parameter is a first gait parameter, wherein the method further comprises determining a second gait parameter corresponding to a shank angle.

Clause 51. The method of Clause 50, wherein the type of gait corresponds to the user shifting a weight of the user forwards or shifting the weight of the user backwards.

Clause 52. The method of any of Clauses 42 to 51, wherein the POD comprises a prosthetic knee.

Clause 53. The method of any of Clauses 42 to 52, wherein the POD comprises a prosthetic foot.

Clause 54. A non-transitory computer-readable storage medium storing instructions, which, when executed on a processor, performs an operation for improving interactions with a prosthetic or orthotic device (POD) by visually outputting information regarding left-right weight shifting of the POD, the operation comprising:

graphically displaying on a graphical user interface (GUI) information indicative of an amount of load placed on the POD, an amount of load placed on the sound limb, and/or a load distribution between the POD and the sound limb; and based on a determination that a threshold weight distribution threshold is satisfied, providing a graphical indicator on the GUI.

Clause 55. The computer-readable storage medium of Clause 54, wherein the graphical user interface is provided on a monitoring device comprising a processor.

Clause 56. The computer-readable storage medium of Clause 55, wherein the processor receives sensor data obtained from a sensor module associated with the POD and processes the sensor data to determine the amount of load placed on the POD, the amount of load placed on the sound limb, and/or the load distribution between the POD and the sound limb.

Clause 57. The computer-readable storage medium of any one of Clauses 54-56, wherein the operation further comprises graphically displaying a timing indicator over which the user is to maintain the threshold weight distribution.

Clause 58. The computer-readable storage medium of any one of Clauses 54-57, wherein the operation further comprises graphically displaying a first shaded region representing the amount of load placed on the POD and a second shaded region representing the amount of load placed on the sound limb, wherein a relative size of the shaded regions indicates the load distribution between the POD and the sound limb.

Clause 59. The computer-readable storage medium of Clause 58, wherein the graphical indicator indicates the amount of shading the user should meet in order to satisfy the threshold weight distribution.

Clause 60. A monitoring device for visually displaying to a user of a prosthetic or orthotic device (POD) information regarding weight distribution between the POD and a sound limb of the user information, the monitoring device comprising a graphical user interface and a software application comprising instructions thereon that when executed causes the software application to perform the steps of any one of Clauses 54-59.

Clause 61. A method for visually displaying to a user of a prosthetic or orthotic device (POD) information regarding weight distribution between the POD and a sound limb of the user information, the method comprising the steps of any one of Clauses 54-59.

Clause 62. A non-transitory computer-readable storage medium storing instructions, which, when executed on a processor, performs an operation for improving interactions with a prosthetic or orthotic device (POD) by visually outputting information regarding forward-backward weight shifting of the POD, the operation comprising:

graphically displaying on a graphical user interface a graphical indication including a load indicator indicative of an amount of load placed on the POD and/or the user's inter-foot weight distribution, and/or an orientation indicator indicative of a shank angle or one or more orientation or weight distribution characteristics; and providing a graphical indicator on the graphical user interface when a threshold transition from loading of the heel to loading of the toe, or vice versa, is satisfied.

Clause 63. A monitoring device for visually displaying to a user of a prosthetic or orthotic device (POD) information regarding weight distribution between the POD and a sound limb of the user information, the monitoring device comprising a graphical user interface and a software application comprising instructions thereon that when executed causes the software application to perform the steps of Clause 63.

Clause 64. A method for visually displaying to a user of a prosthetic or orthotic device (POD) information regarding weight distribution between the POD and a sound limb of the user information, the method comprising the steps Clause 63.

Clause 65. A method of performing any of Clauses 1-40.

Clause 66. A non-transitory computer-readable storage medium storing instructions, which, when executed on a processor, performs an operation for improving interactions with a prosthetic or orthotic device (POD), the operation comprising any of the steps of Clauses 1-54.

Clause 67. A non-transitory computer-readable storage medium storing instructions, which, when executed on a processor, performs an operation for improving interactions with a prosthetic or orthotic device (POD), the operation comprising one or more of the steps or features of the foregoing description drawings.

Clause 68. A method for improving interactions with a prosthetic or orthotic device (POD), the method comprising one or more of the steps or features of the foregoing description or drawings.

Clause 69. A system for improving interactions with a prosthetic or orthotic device (POD), the system comprising one or more of the features of the foregoing description or drawings.

Clause 70. A monitoring device for improving interactions with a prosthetic or orthotic device (POD), the monitoring device comprising one or more of the features of the foregoing description or drawings.

Terminology

Although this disclosure has been described in the context of certain embodiments and examples, it will be understood by those skilled in the art that the disclosure extends beyond the specifically disclosed embodiments to other alternative embodiments and/or uses and obvious modifications and equivalents thereof. In addition, while several variations of the embodiments of the disclosure have been shown and described in detail, other modifications, which are within the scope of this disclosure, will be readily apparent to those of skill in the art. It is also contemplated that various combinations or sub-combinations of the specific features and aspects of the embodiments may be made and still fall within the scope of the disclosure. For example, features described above in connection with one embodiment can be used with a different embodiment described herein and the combination still fall within the scope of the disclosure. It should be understood that various features and aspects of the disclosed embodiments can be combined with, or substituted for, one another in order to form varying modes of the embodiments of the disclosure. Thus, it is intended that the scope of the disclosure herein should not be limited by the particular embodiments described above. Accordingly, unless otherwise stated, or unless clearly incompatible, each embodiment of this invention may include, additional to its essential features described herein, one or more features as described herein from each other embodiment of the invention disclosed herein.

Features, materials, characteristics, or groups described in conjunction with a particular aspect, embodiment, or example are to be understood to be applicable to any other aspect, embodiment or example described in this section or elsewhere in this specification unless incompatible there-with. All of the features disclosed in this specification (including any accompanying claims, abstract and drawings), and/or all of the steps of any method or process so disclosed, may be combined in any combination, except combinations where at least some of such features and/or steps are mutually exclusive. The protection is not restricted to the details of any foregoing embodiments. The protection extends to any novel one, or any novel combination, of the features disclosed in this specification (including any accompanying claims, abstract and drawings), or to any novel one, or any novel combination, of the steps of any method or process so disclosed.

Furthermore, certain features that are described in this disclosure in the context of separate implementations can also be implemented in combination in a single implementation. Conversely, various features that are described in the context of a single implementation can also be implemented in multiple implementations separately or in any suitable subcombination. Moreover, although features may be described above as acting in certain combinations, one or more features from a claimed combination can, in some cases, be excised from the combination, and the combination may be claimed as a subcombination or variation of a subcombination.

Moreover, while operations may be depicted in the drawings or described in the specification in a particular order, such operations need not be performed in the particular order shown or in sequential order, or that all operations be performed, to achieve desirable results. Other operations that are not depicted or described can be incorporated in the example methods and processes. For example, one or more additional operations can be performed before, after, simultaneously, or between any of the described operations. Further, the operations may be rearranged or reordered in other implementations. Those skilled in the art will appreciate that in some embodiments, the actual steps taken in the processes illustrated and/or disclosed may differ from those shown in the figures. Depending on the embodiment, certain of the steps described above may be removed, others may be added. Furthermore, the features and attributes of the specific embodiments disclosed above may be combined in different ways to form additional embodiments, all of which fall within the scope of the present disclosure. Also, the separation of various system components in the implementations described above should not be understood as requiring such separation in all implementations, and it should be understood that the described components and systems can generally be integrated together in a single product or packaged into multiple products.

For purposes of this disclosure, certain aspects, advantages, and novel features are described herein. Not necessarily all such advantages may be achieved in accordance with any particular embodiment. Thus, for example, those skilled in the art will recognize that the disclosure may be embodied or carried out in a manner that achieves one advantage or a group of advantages as taught herein without necessarily achieving other advantages as may be taught or suggested herein.

Conditional language, such as "can," "could," "might," or "may," unless specifically stated otherwise, or otherwise understood within the context as used, is generally intended to convey that certain embodiments include, while other embodiments do not include, certain features, elements, and/or steps. Thus, such conditional language is not generally intended to imply that features, elements, and/or steps are in any way required for one or more embodiments or that one or more embodiments necessarily include logic for deciding, with or without user input or prompting, whether these features, elements, and/or steps are included or are to be performed in any particular embodiment.

Conjunctive language such as the phrase "at least one of X, Y, and Z," unless specifically stated otherwise, is otherwise understood with the context as used in general to convey that an item, term, etc. may be either X, Y, or Z. Thus, such conjunctive language is not generally intended to imply that certain embodiments require the presence of at least one of X, at least one of Y, and at least one of Z.

Language of degree used herein, such as the terms "approximately," "about," "generally," and "substantially" as used herein represent a value, amount, or characteristic close to the stated value, amount, or characteristic that still performs a desired function or achieves a desired result. For example, the terms "approximately", "about", "generally," and "substantially" may refer to an amount that is within less than 10% of, within less than 5% of, within less than 1% of, within less than 0.1% of, and within less than 0.01% of the stated amount. As another example, in certain embodiments, the terms "generally parallel" and "substantially parallel" refer to a value, amount, or characteristic that departs from exactly parallel by less than or equal to 15 degrees, 10 degrees, 5 degrees, 3 degrees, 1 degree, 0.1 degree, or otherwise.

The scope of the present disclosure is not intended to be limited by the specific disclosures of preferred embodiments in this section or elsewhere in this specification, and may be defined by claims as presented in this section or elsewhere in this specification or as presented in the future. The language of the claims is to be interpreted broadly based on the language employed in the claims and not limited to the examples described in the present specification or during the prosecution of the application, which examples are to be construed as non-exclusive.

What is claimed is:

1. A system for improving interactions with a prosthetic or orthotic device (POD), the system comprising:
   the POD comprising:
      a first limb member,
      a second limb member coupled to the first limb member via a joint, and
      a sensor module configured to measure one or more parameters relating to the POD; and
   a monitoring device configured to be in wireless communication with the POD and configured to:
      receive gait parameter data from the POD over time based at least in part on sensor data over the time,
      generate in real time a graphical user interface (GUI) that displays a graphical indication of a gait parameter over the time,
      compare the gait parameter with a gait parameter threshold, and
      based on a determination that the gait parameter satisfies the gait parameter threshold, cause display on the GUI of an indicator indicating the gait parameter threshold is satisfied.

2. The system of claim 1, wherein the POD comprises a prosthetic knee, wherein the sensor module is configured to measure the one or more parameters during locomotion of a user fitted with the POD, wherein the locomotion corresponds to at least one of the user shifting weight from the POD to a sound limb, the user shifting weight from the sound limb to the POD, the user shifting weight from a toe of the POD to a heel of the POD, the user shifting weight from the heel of the POD to the toe of the POD, the user sitting down, the user descending stairs, the user ascending stairs, a user shifting body weight forward, or a user shifting body weight backward.

3. The system of claim 1, wherein the sensor module comprises a force sensor configured to measure an amount of load on the POD, wherein the gait parameter corresponds to the amount of load on the POD, wherein the gait parameter threshold comprises a load threshold corresponding to the amount of load placed on the POD, and wherein said causing display on the GUI of the indicator is further based on a determination that the gait parameter satisfies the gait parameter threshold for a threshold period of time.

4. The system of claim 3, wherein the load threshold corresponds to a portion of a user's body weight.

5. The system of claim 3, wherein the sensor module further comprises a sensor configured to measure at least one of a braking torque applied by the POD, a braking power applied by the POD, a resistance provided by the POD, or a current flowing through the POD.

6. The system of claim 5, wherein the gait parameter is a first gait parameter, wherein the graphical indication is a first graphical indication, wherein the GUI displays a second graphical indication of a second gait parameter over the time, wherein the second gait parameter corresponds to the at least one of the braking torque applied by the POD, the braking power applied by the POD, the resistance provided by the POD, or the current flowing through the POD, wherein the monitoring device is further configured to:
  compare the second gait parameter with a resistance threshold; and
  based on a determination that the second gait parameter satisfies the resistance threshold, cause display on the GUI of an indicator indicating the resistance threshold is satisfied.

7. The system of claim 6, wherein the sensor module further comprises an angle sensor configured to measure a joint angle corresponding to an angle between the first limb member and the second limb member, wherein the GUI displays the second graphical indication in response to a determination that the joint angle satisfies a first angle threshold and does not satisfy a second angle threshold.

8. The system of claim 3, wherein the sensor module further comprises at least one of an acceleration sensor or an orientation sensor.

9. The system of claim 8, wherein the gait parameter is a first gait parameter, wherein the graphical indication is a first graphical indication, wherein the GUI displays a second graphical indication of a second gait parameter over the time, wherein the second gait parameter corresponds to a shank angle based on the data from the at least one of the acceleration sensor or the orientation sensor, wherein the monitoring device is further configured to:
  compare the second gait parameter with a first shank angle threshold and second shank angle threshold; and
  based on a determination that, over the time, the first shank angle threshold was satisfied and the second shank angle threshold was satisfied, cause display on the GUI of an indicator indicating the first shank angle threshold and second shank angle threshold were satisfied.

10. The system of claim 9, wherein the first shank angle threshold corresponds to load on a heel the POD and the second shank angle threshold corresponds to load on a toe of the POD.

11. A method for improving interactions with a prosthetic or orthotic device (POD), the method comprising:
  receiving gait parameter data from the POD over time based at least in part on sensor data over the time, wherein the POD comprises:
    a first limb member,
    a second limb member coupled to the first limb member via a joint, and
    a sensor module configured to measure one or more parameters relating to the POD; and
  generating in real time a graphical user interface (GUI) that displays a graphical indication of a gait parameter over the time,
  comparing the gait parameter with a gait parameter threshold, and
  based on a determination that the gait parameter satisfies the gait parameter threshold, causing display on the GUI of an indicator indicating the gait parameter threshold is satisfied.

12. The method of claim 11, wherein the sensor module comprises a force sensor configured to measure an amount of load on the POD, wherein the gait parameter corresponds to the amount of load on the POD, wherein the gait parameter threshold comprises a load threshold corresponding to the amount of load placed on the POD, and wherein said causing display on the GUI of the indicator is further based on a determination that the gait parameter satisfies the gait parameter threshold for a threshold period of time.

13. The method of claim 12, wherein the gait parameter is a first gait parameter, wherein the graphical indication is a first graphical indication, wherein the GUI displays a second graphical indication of a second gait parameter over the time, wherein the second gait parameter corresponds to at least one of a braking torque applied by the POD, a braking power applied by the POD, a resistance provided by the POD, or a current flowing through the POD, the method further comprising:
  comparing the second gait parameter with a resistance threshold; and
  based on a determination that the second gait parameter satisfies the resistance threshold, causing display on the GUI of an indicator indicating the resistance threshold is satisfied.

14. The method of claim 13, wherein the sensor module further comprises an angle sensor configured to measure a joint angle corresponding to an angle between the first limb member and the second limb member, wherein said causing display on the GUI of the indicator indicating the resistance threshold is satisfied is in response to a determination that the joint angle satisfies a first angle threshold and does not satisfy a second angle threshold.

15. The method of claim 11, wherein the sensor module further comprises at least one of an acceleration sensor or an orientation sensor, wherein the gait parameter is a first gait parameter, wherein the graphical indication is a first graphical indication, wherein the GUI displays a second graphical indication of a second gait parameter over the time, wherein the second gait parameter corresponds to a shank angle based on the data from the at least one of the acceleration sensor or the orientation sensor, the method further comprising:
  comparing the second gait parameter with a first shank angle threshold and second shank angle threshold, wherein the first shank angle threshold corresponds to load on a heel the POD and the second shank angle threshold corresponds to load on a toe of the POD; and
  based on a determination that, over the time, the first shank angle threshold was satisfied and the second shank angle threshold was satisfied, causing display on the GUI of an indicator indicating the first shank angle threshold and second shank angle threshold were satisfied.

16. A non-transitory computer-readable storage medium storing instructions, which, when executed on a processor, performs an operation for improving interactions with a prosthetic or orthotic device (POD), the operation comprising:
receiving gait parameter data from the POD over time based at least in part on sensor data over the time, wherein the POD comprises:
a first limb member,
a second limb member coupled to the first limb member via a joint, and
a sensor module configured to measure one or more parameters relating to the POD;
generating in real time a graphical user interface (GUI) that displays a graphical indication of a gait parameter over the time;
comparing the gait parameter with a gait parameter threshold; and
based on a determination that the gait parameter satisfies the gait parameter threshold, causing display on the GUI of an indicator indicating the gait parameter threshold is satisfied.

17. The computer-readable storage medium of claim 16, wherein the sensor module comprises a force sensor configured to measure an amount of load on the POD, wherein the gait parameter corresponds to the amount of load on the POD, wherein the gait parameter threshold comprises a load threshold corresponding to the amount of load placed on the POD, and wherein said causing display on the GUI of the indicator is further based on a determination that the gait parameter satisfies the gait parameter threshold for a threshold period of time.

18. The computer-readable storage medium of claim 17, wherein the gait parameter is a first gait parameter, wherein the graphical indication is a first graphical indication, wherein the GUI displays a second graphical indication of a second gait parameter over the time, wherein the second gait parameter corresponds to at least one of a braking torque applied by the POD, a braking power applied by the POD, a resistance provided by the POD, or a current flowing through the POD, the operation further comprising:
comparing the second gait parameter with a resistance threshold; and
based on a determination that the second gait parameter satisfies the resistance threshold, causing display on the GUI of an indicator indicating the resistance threshold is satisfied.

19. The computer-readable storage medium of claim 18, wherein the sensor module further comprises an angle sensor configured to measure a joint angle corresponding to an angle between the first limb member and the second limb member, wherein said causing display on the GUI of the indicator indicating the resistance threshold is satisfied is in response to a determination that the joint angle satisfies a first angle threshold and does not satisfy a second angle threshold.

20. The computer-readable storage medium of claim 16, wherein the sensor module further comprises at least one of an acceleration sensor or an orientation sensor, wherein the gait parameter is a first gait parameter, wherein the graphical indication is a first graphical indication, wherein the GUI displays a second graphical indication of a second gait parameter over the time, wherein the second gait parameter corresponds to a shank angle based on the data from the at least one of the acceleration sensor or the orientation sensor, the operation further comprising:
comparing the second gait parameter with a first shank angle threshold and second shank angle threshold, wherein the first shank angle threshold corresponds to load on a heel the POD and the second shank angle threshold corresponds to load on a toe of the POD; and
based on a determination that, over the time, the first shank angle threshold was satisfied and the second shank angle threshold was satisfied, causing display on the GUI of an indicator indicating the first shank angle threshold and second shank angle threshold were satisfied.

* * * * *